(12) United States Patent
Hubbell et al.

(10) Patent No.: US 7,060,681 B2
(45) Date of Patent: Jun. 13, 2006

(54) COMPOSITIONS AND METHODS FOR USE OF BIOACTIVE AGENTS DERIVED FROM SULFATED AND SULFONATED AMINO ACIDS

(75) Inventors: Jeffrey A. Hubbell, Zurich (CH); Ronald Schoenmakers, Zurich (CH); Heather D. Maynard, Santa Monica, CA (US)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 415 days.

(21) Appl. No.: 10/201,547

(22) Filed: Jul. 22, 2002

(65) Prior Publication Data

US 2003/0064410 A1 Apr. 3, 2003

Related U.S. Application Data

(60) Provisional application No. 60/306,726, filed on Jul. 20, 2001.

(51) Int. Cl.
*A61K 38/00* (2006.01)
(52) U.S. Cl. .......................... 514/12; 530/300
(58) Field of Classification Search ..................... None
See application file for complete search history.

(56) References Cited

U.S. PATENT DOCUMENTS 6,037,329 A 3/2000 Baird et al.

FOREIGN PATENT DOCUMENTS

| WO | WO 01/98365 | 12/2001 |
|----|-------------|---------|
| WO | WO 2005/034844 | 4/2005 |

OTHER PUBLICATIONS

Folkman et al "Control of angiogenesis with synthetic heparin substitutes" Science, 1989, vol. 243, No. 4897, pp. 1490-1493.*
Heather D. Maynard and Jeffrey A. Hubbell, "Identification of oligopeptide VEGF binders using a rationally designed combinatorial library approach", Abstract for Chicago ACS Meeting, Aug. 2001, Chicago, Illinois.
Heather D. Maynard and Jeffrey A. Hubbell, "Discovery of Novel Oligopeptides for Controlled Release of Therapeutic Molecules Using a Rationally Designed Combinatorial Library Approach", Poster, Plymouth, New Hampshire, Jul. 2001.
Kit S. Lam, "Application of Combinatorial library methods in cancer research and drug discovery", *Anti-Cancer Drug Design* (1997), vol. 12, pp. 145-167.
Sandra Liekens, Daria Leali, Johan Neyts, Robert Esnouf, Marco Rusnati, Patrizia Dell'Era, Prabhat C. Maudgal, Erik De Clercq, and Marco Presta, "Modulation of Fibroblast Growth Factor-2 Receptor Binding, Signaling, and Mitogenic Activity by Heparin-Mimicking Polysulfonated Compounds", *Molecular Pharmacology* (1999), vol. 56, pp. 204-213.
Christopher R. Parish, Craig Freeman, Kathryn J. Brown, Douglas J. Francis and William B. Cowden, "Identification of Sulfated Oligosaccharide-based Inhibitors of Tumor Growth and Metastasis Using Novel *in Vitro* Assays for Angiogenesis and Heparanase Activity", *Cancer Research*, vol. 59, pp. 3433-3441.
Gerhard Zugmaier, Marc E. Lippman and Anton Wellstein, "Inhibition by Pentosan Polysulfate (PPS) of Heparin-Binding Growth Factors Released From Tumor Cells and Blockage by PPS of Tumor Growth in Animals", *Journal of the National Cancer Institute*, vol. 84, No. 22, Nov. 18, 1992, pp. 1716-1724.
Judah Folkman, Paul B. Weisz, Madeleine M. Joullié, William W. Li and William R. Ewing, "Control of Angiogenesis with Synthetic Heparin Substitutes", *Science*, vol. 241, pp. 1490-1493.
Constant A. A. van Boeckel and Maurice Petitou, "The Unique Antithrombin III Binding Domain of Heparin: A Lead to New Synthetic Antithrombotics", *Angewandte Chemie* (International Edition in English), vol. 32, No. 12, pp. 1671-1690.
E. de Raucourt, S. Mauray, F. Chaubet, O. Maiga-Revel, M. Jozefowics, A.M. Fischer, "Anticoagulant activity of dextran derivatives", 1998.
Brett Feret, "A novel synthetic antithrombotic for prevention of venous thromboemblism", *Formulary*, Dec. 2001, vol. 36, pp. 831-837.
J.M. Herbert, J.P. Hérault, A. Bernat, R.G.M. van Amsterdam, J.C. Lormeau, M. Petitou, C. van Boeckel, P. Hoffmann, and D.G. Meuleman, "Biochemical and Pharmacological Properties of SANORG 34006, a Potent and Long-Acting Synthetic Pentasaccharide", *Blood*, vol. 91, No. 11, (Jun. 1, 1998), pp. 4197-4205.
Delphine Logeart-Avramoglou, Jacqueline Jozefonvicz, "Carboxymethyl Benzylamide Sulfonate Dextrans (CMDBS), A Family of Biospecific Polymers Endowed with Numerous Biological Properties: A Review", pp. 578-590.

(Continued)

*Primary Examiner*—Bruce R. Campell
*Assistant Examiner*—Roy Teller
(74) *Attorney, Agent, or Firm*—Patterson, Thuente, Skaar & Christensen, P.A.

(57) ABSTRACT

The application describes ligands for binding targets, the ligands preferably including peptides having at least one sulfated or sulfonated amino acid. The ligand preferably specifically binds to heparin binding sites of biomolecules. Compositions, systems, and methods for making and using the ligands are described.

15 Claims, 6 Drawing Sheets

OTHER PUBLICATIONS

J.M. Herbert, J.P. Hérault, A. Bernat, R.G.M. van Amsterdam, G.M.T. Vogel, J.C. Lormeau, M. Petitou and D.G. Meuleman, "Biochemical and Pharmacological Properties of SANORG 32701", *American Heart Research*, Circulation Report, vol. 79, No. 3.

J.R. Fromm, R.E. Hileman, E.E.O. Caldwell, J.M. Weiler, and R.J. Linhardt, "Pattern of Spacing of Basic Amino Acids in Heparin Binding Sites", *Archives of Biochemistry and Biophysics*, vol. 343, No. 1, pp. 92-100.

Alfonso Bentolila, Israel Vlodavsky, Christine Haloun and Abraham J. Domb, "Synthesis and Heparin-like Biological Activity of Amino Acid-based Polymers", *Polymers for Advanced Technologies*, vol. 11, (2000), pp. 377-387.

Socorro Vázquez Campos, Les P. Miranda and Morten Meldal, "Preparation of novel O-sulfated amino acid building blocks with improved acid stability for Fmoc-based solid-phase peptide synthesis," *The Royal Society of Chemistry*, 2002, pp. 682-686.

Hua-Quan Miao, David M. Ornitz, Elena Aingorn, Shmuel A. Ben-Sasson, and Israel Vlodavsky, "Modulation of Fibroblast Growth Factor-2 Receptor Binding, Dimerization, Signaling and Angiogenic Activity by a Synthetic Heparin-mimicking Polyanionic Compound", *The Journal of Clinical Investigation*, vol. 99, No. 7, pp. 1565-1575.

Ryo Muramatsu, Masashi Sasaki, Nobuo Watanabe, Yuso Goto, Toru Okayama, Eriko Nukui, Tadanori Morikawa and Hideya Hayashi, "Antithrombotic Effects of NF-6505, A Novel Anion-Binding Exosite Inhibitor", *Thrombosis Research*, vol. 86, No. 6, pp. 453-460.

Wayne J. Fairbrother, Hans W. Christinger, Andrea G. Cochran, Germaine Fuh, Christopher J. Keenan, Clifford Quan, Stephanie K. Shirver, Jeffrey Y.K. Tom, James A. Wells, and Brian C. Cunningham, "Novel Peptides Selected to Bind Vascular Endothelial Growth Factor Target the Receptor-Binding Site", *Biochemistry*, vol. 37, pp. 17754-17764.

Ruth Tyler-Cross, Michael Sobel, Dalila Marques, and Robert B. Harris, "Heparin binding domain peptides of antithrombin III: Analysis by isothermal titration calorimetry and circular dichroism spectroscopy", *Protein Science*, vol. 3, (1994), pp. 620-627.

Jack Hirsh, MD, Sonia S. Anand, MD, Jonathan L. Halperin, MD and Valentin Fuster, MD, Ph.D, "Guide to Anticoagulant Therapy: Heparin A Statement for Healthcare Professionals From the American Heart Association", *American Heart Association, Inc.*, Circulation, vol. 103, pp. 2994-3018.

Gideon Bosker, MD FACEP, "Current Versus Future Strategies for Prevention of DVT in Patients Undergoing Hip and Knee Surgery", *Orthopedic Clinical Consensus Reports*, Oct. 12, 2001, pp. 1-12.

Gera Neufeld, Tzafra Cohen, Stela Gengrinovitch, and Zoya Poltorak, "Vascular endothelial growth factor (VEGF) and its receptors", *The FASEB Journal*, vol. 13, Jan. 1999, pp. 9-22.

Fatima El Khadali, Gárard Hélary, Graciela Pavon-Djavid, and Véronique Migonney, "Modulating Fibroblast Cell Proliferation with Functionalized Poly(methyl metacrylate) Based Copolymers: Chemical Compositions and Monomer Distribution Effect", *Biomacromolecules*, vol. 3, No. 1, 2002, pp. 51-56.

Hyman Engelberg, M.D., "Actions of Heparin That May Affect The Malignant Process", *Cancer*, vol. 85, No. 2, Jan. 15, 1999, pp. 257-272.

Roseyyne Binétry-Tournaire, Caroline Demangel, Bernard Malavaud, Roger Vassy, Sylvie Rouyre, Michael Kraemer, Jean Plouët, Claude Derbin, Gérard Perret and Jean Claude Mazié, "Identification of a peptide blocking vascular endothelial growth factor (VEGF)-mediated angiogenesis", *The EMBO Journal*, vol. 19, No. 7, pp. 1525-1533.

Ishan Capila and Robert J. Linhardt, "Hearpin-Protein Interactions", *Angew. Chem. Int. Ed.*, vol. 41, 2002, pp. 390-412.

Massimo Cristofanilli, Chusilp Charnsangavej and Garbriel N. Hortobagyi, "Angiogenesis Modulation in Cancer Research: Novel Clinical Approaches", *Nature Reviews*, vol. 1, Jun. 2002, pp. 415-426.

Rosa Crum, Sandor Szabo, and Judah Folkman, "A New Class of Steroids Inhibits Angiogenesis in the Presence of Heparin or a Heparin Fragment", *Science*, vol. 230, Dec. 20, 1985, pp. 1375-1378.

R. Danesi, S. Del Bianchi, P. Soldani, A. Campagni, R.V. La Rocca, C.E. Myers, A. Paparelli & M. Del Tacca, "Suramin inhibits bFGF-induced endothelial cell proliferation and angiogenesis in the chick chorioallantoic membrane", *Cancer*, vol. 68, pp. 932-938.

Sandra Liekens, Johan Neyts, Bart Degrève, and Erik De Clercq, "The Solfonic Acid Polymers PAMPS [Poly(2-Acrylamido-2-Methyl-1-Propanesulfonic Acid)] and Related Analogues Are Highly Potent Inhibitors of Angiogenesis", *Oncology Research*, vol. 9, 1997, pp. 173-181.

Angela Firsching, Peter Nickel, Particia Mora, and Bruno Allolio, "Antiproliferative and Angiostatic Activity of Suramin Analogues", *Cancer Research*, vol. 55, Nov. 1, 1995, pp. 4957-4961.

Anton Wellstein and Frank Czubayko, "Inhibition of Fibroblat Growth Factors", *Breast Cancer Research and Treatment*, vol. 38, 1996, pp. 109-119.

Zoltan Szekanecz, Margaret M. Halloran, Catherine J. Haskell, Manisha R. Shah, Peter J. Polverini, and Alisa E. Koch, "Mediators of Angiogenesis: The Role of Cellular Adhesion Molecules", *Trends in Clycoscience and Glycotechnology*, vol. 11, No. 58, Mar. 1999, pp. 73-93.

J. Drevs, A. Droll, K. Mross, and C. Unger "Angiogenesis Inhibition: Drugs in Clinical Trials", *Onkologie*, vol. 22, 1999, pp. 282-290.

Carlberg et al., "Specific binding of D-Tyr$^{25}$(Nle$^{28,31}$)-CCK(25-33) to cortical membranes from rat brain", *Neuroscience Letters*, 122:29-32 (1991).

Muramatsu et al., "Antithrombotic Effects of NF-6505, A Novel Anion-Binding Exosite Inhibitor", *Thrombosis Research*, 86(6):453-460 (1997).

\* cited by examiner

PATTERN AND SPACING OF AMINO ACIDS IN HEPARIN

| Target | Heparin-Binding Peptide Sequences |
|---|---|
| bFGF | FFFERLESNNYNTYRSRKYSSWYVALKR |
| Antistasin | PNGLKRDKLGCEYCECRPKRKLIPRLS |
| Apo E | LRKRLLRD |
|  | GERLRARM |
| LPL | RKNRCNNLGYEINKVRAKR |
| EC-SOD | REHSERKKRRRESECKAA |
| vWF | YIGLKDRKRPSELRRIASQVKYA |
| NCAM | TWKHKGRDVILKKDVRFI |
| Fibronectin | RRARVTDATETTITISWRTKETETITGFQVDAIPANG |
|  | YEKPGSPPREVVPRPRPGV |
|  | KNNQKSEPLIGRKKT |
| Laminin | RYVVLPRPVCFEKGMNYTVR |
|  | RIQNLLKITNLRIKFVK |
|  | KQNCLSSRASFRGCVRNLRLSR |
| Vitronectin | AKKQRFRHRNRKGYR |
| ATIII | AKLNCRLYRKANKSSKLVSANR |
| PF4 | KDGRKICLDLQAPLYKKIIKKLLES |
| L-type C channel | KGKMHKTCYY |
|  | MGKMHKTCYN |
| aFGF | KKHEAKNWFVGLKKGSCKRGP |
| Protein C inhibitor | SEKTLRKWLKMFKKRQLELY |
| 90-kDa stress protein | LYVR |
|  | LRQK |
| Trombospondin | RKGSGRRLVK |
|  | RQMKKTR |
| TGF β1 | DFRKDLGWKWIHEPKGYHA |
| Apo B100 | LSVKAQYKKNKHRHSI |
|  | YKLEGTTRLTRKRGLKLATA |
| PDGF-A | GRPRESGKKRKRKRLKPT |
| Xanthine oxidase | LGVPANRIVVRVKRM |
|  | KKKNPSGSWEDWVTAAY |
| Glia derived nexin | RYNVNGVGKVLKKINKAIVSKKNK |
| TFPI | GKCRPFKYSGCGGNENNFTSKQECLRACKKGF |
| AAMP | RRLRRMESESES |
| IGFBP-5 | RKGFYKRKQCKPSRGRK |
| IGFBP-3 | KKGFYKKKQCRPSKGRKR |
| HB-EGF | KRKKKGKGLGKKRDPCLRKYK |

FIG. 2

| SEQ ID NO. | SEQUENCE |
|---|---|
| 1. | YDY |
| 2. | SYDY |
| 3. | AYDY |
| 4. | SYYF |
| 5. | GYYF |
| 6. | SYAY |
| 7. | GYAY |
| 8. | GYVE |
| 9. | DYYY |
| 10. | GYSE |
| 11. | SVFVSXXXSX |
| 12. | SVFVSSVVSS |
| 13. | FYGGYDY |
| 14. | YYGGYDY |
| 15. | AYGGYDY |
| 16. | YYGGYDYG |
| 17. | SYDYG |
| 18. | YVVYYXXXYX |
| 19. | SVFSSXXXSX |
| 20. | SVSFSXXXSX |
| 21. | SFSVSXXXSX |
| 22. | SSSVSXXXSX |
| 23 | SVFVSFVGSS |
| 24. | SVFVSFGVSS |

* "X" stands for any single amino acid

FI

SEQUENCE LISTING

<160> NUMBER OF SEQ ID NOS: 24

<210> SEQ ID NO 1
<211> LENGTH: 3
<212> TYPE: PRT
<213> ORGANISM: Artificial Sequence -continued

```
<220> FEATURE:
<223> OTHER INFORMATION: A ligand for binding a target biomolecule
<220> FEATURE:
<221> NAME/KEY: PEPTIDE
<222> LOCATION: (1)..(3)
<223> OTHER INFORMATION:

<400> SEQUENCE: 1

Tyr Asp Tyr
1

<210> SEQ ID NO 2
<211> LENGTH: 4
<212> TYPE: PRT
<213> ORGANISM: Artificial sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 2

Ser Tyr Asp Tyr
1

<210> SEQ ID NO 3
<211> LENGTH: 4
<212> TYPE: PRT
<213> ORGANISM: Artificial sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 3

Ala Tyr Asp Tyr
1

<210> SEQ ID NO 4
<211> LENGTH: 4
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 4

Ser Tyr Tyr Phe
1

<210> SEQ ID NO 5
<211> LENGTH: 4
<212> TYPE: PRT
<213> ORGANISM: Artificial Sequence
<220> FEATURE:
<223> OTHER INFORMATION: A ligand for binding a target biomolecule

<400> SEQUENCE: 5

Gly Tyr Tyr Phe
1
```

```
<210> SEQ ID NO 6
<211> LENGTH: 4
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 6

Ser Tyr Ala Tyr
1

<210> SEQ ID NO 7
<211> LENGTH: 4
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 7

Gly Tyr Ala Tyr
1

<210> SEQ ID NO 8
<211> LENGTH: 4
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 8

Gly Tyr Val Glu
1

<210> SEQ ID NO 9
<211> LENGTH: 4
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:

<400> SEQUENCE: 9

Asp Tyr Tyr Tyr
1

<210> SEQ ID NO 10
<211> LENGTH: 4
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(4)
<223> OTHER INFORMATION:
```

```
<400> SEQUENCE: 10

Gly Tyr Ser Glu
1

<210> SEQ ID NO 11
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: MISC_FEATURE
<222> LOCATION: (6)..(8)
<223> OTHER INFORMATION: xaa may be any amino acid
<220> FEATURE:
<221> NAME/KEY: MISC_FEATURE
<222> LOCATION: (10)..(10)
<223> OTHER INFORMATION: xaa may be any amino acid

<400> SEQUENCE: 11

Ser Val Phe Val Ser Xaa Xaa Xaa Ser Xaa
1               5                   10

<210> SEQ ID NO 12
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:

<400> SEQUENCE: 12

Ser Val Phe Val Ser Ser Val Val Ser Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: A  ligand for binding a target biomolecule
<220> FEATURE:
<221> NAME/KEY: PEPTIDE
<222> LOCATION: (1)..(7)
<223> OTHER INFORMATION:

<400> SEQUENCE: 13

Phe Tyr Gly Gly Tyr Asp Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: A  ligand for binding a target biomolecule
<220> FEATURE:
<221> NAME/KEY: PEPTIDE
<222> LOCATION: (1)..(7)
<223> OTHER INFORMATION:

<400> SEQUENCE: 14

Tyr Tyr Gly Gly Tyr Asp Tyr
1               5
```

```
<210> SEQ ID NO 15
<211> LENGTH: 7
<212> TYPE: PRT
<213> ORGANISM: Artificial Sequence
<220> FEATURE:
<223> OTHER INFORMATION: A  ligand for binding a target biomolecule
<220> FEATURE:
<221> NAME/KEY: PEPTIDE
<222> LOCATION: (1)..(7)
<223> OTHER INFORMATION:

<400> SEQUENCE: 15

Ala Tyr Gly Gly Tyr Asp Tyr
1               5

<210> SEQ ID NO 16
<211> LENGTH: 8
<212> TYPE: PRT
<213> ORGANISM: Artificial  Sequence
<220> FEATURE:
<223> OTHER INFORMATION: A  ligand for binding a target biomolecule
<220> FEATURE:
<221> NAME/KEY: PEPTIDE
<222> LOCATION: (1)..(8)
<223> OTHER INFORMATION:

<400> SEQUENCE: 16

Tyr Tyr Gly Gly Tyr Asp Tyr Gly
1               5

<210> SEQ ID NO 17
<211> LENGTH: 5
<212> TYPE: PRT
<213> ORGANISM: Artificial Sequence
<220> FEATURE:
<223> OTHER INFORMATION: A  ligand for binding a target biomolecule

<400> SEQUENCE: 17

Ser Tyr Asp Tyr Gly
1               5

<210> SEQ ID NO 18
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:
<220> FEATURE:
<221> NAME/KEY: MISC_FEATURE
<222> LOCATION: (6)..(8)
<223> OTHER INFORMATION: Xaa  may be any amino acid
<220> FEATURE:
<221> NAME/KEY: MISC_FEATURE
<222> LOCATION: (10)..(10)
<223> OTHER INFORMATION: Xaa  may be any amino acid

<400> SEQUENCE: 18

Tyr Val Val Tyr Tyr Xaa Xaa Xaa Tyr Xaa
1               5                   10

<210> SEQ ID NO 19
<211> LENGTH: 10
<212> TYPE: PRT
<213> ORGANISM: Artificial Sequence
<220> FEATURE:
<223> OTHER INFORMATION: A ligand for binding a target biomolecule
```

```
<220> FEATURE:
<221> NAME/KEY: PEPTIDE
<222> LOCATION: (1)..(10)
<223> OTHER INFORMATION:
<220> FEATURE:
<221> NAME/KEY: MISC_FEATURE
<222> LOCATION: (6)..(8)
<223> OTHER INFORMATION: Xaa may be any amino acid
<220> FEATURE:
<221> NAME/KEY: MISC_FEATURE
<222> LOCATION: (10)..(10)
<223> OTHER INFORMATION: Xaa may be any amino acid

<400> SEQUENCE: 19

Ser Val Phe Ser Ser Xaa Xaa Xaa Ser Xaa
1               5                   10

<210> SEQ ID NO 20
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:
<220> FEATURE:
<221> NAME/KEY: MISC_FEATURE
<222> LOCATION: (6)..(8)
<223> OTHER INFORMATION: Xaa may be any amino acid
<220> FEATURE:
<221> NAME/KEY: MISC_FEATURE
<222> LOCATION: (10)..(10)
<223> OTHER INFORMATION: Xaa may be any amino acid

<400> SEQUENCE: 20

Ser Val Ser Phe Ser Xaa Xaa Xaa Ser Xaa
1               5                   10

<210> SEQ ID NO 21
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:
<220> FEATURE:
<221> NAME/KEY: MISC_FEATURE
<222> LOCATION: (6)..(8)
<223> OTHER INFORMATION: Xaa may be any amino acid
<220> FEATURE:
<221> NAME/KEY: MISC_FEATURE
<222> LOCATION: (10)..(10)
<223> OTHER INFORMATION: Xaa may be any amino acid

<400> SEQUENCE: 21

Ser Phe Ser Val Ser Xaa Xaa Xaa Ser Xaa
1               5                   10

<210> SEQ ID NO 22
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:
```

```
<220> FEATURE:
<221> NAME/KEY: MISC_FEATURE
<222> LOCATION: (6)..(8)
<223> OTHER INFORMATION: Xaa may be any amino acid
<220> FEATURE:
<221> NAME/KEY: MISC_FEATURE
<222> LOCATION: (10)..(10)
<223> OTHER INFORMATION: Xaa may be any amino acid

<400> SEQUENCE: 22

Ser Ser Ser Val Ser Xaa Xaa Xaa Ser Xaa
1               5                   10

<210> SEQ ID NO 23
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:

<400> SEQUENCE: 23

Ser Val Phe Val Ser Phe Val Gly Ser Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: A ligand for binding a target biomolecule
<220> FEATURE:
<221> NAME/KEY: PEPTIDE
<222> LOCATION: (1)..(10)
<223> OTHER INFORMATION:

<400> SEQUENCE: 24

Ser Val Phe Val Ser Phe Gly Val Ser Ser
1               5                   10
```

COMPOSITIONS AND METHODS FOR USE OF BIOACTIVE AGENTS DERIVED FROM SULFATED AND SULFONATED AMINO ACIDS

RELATED APPLICATIONS

This application claims priority to U.S. provisional patent application No. 60/306,726 filed Jul. 20, 2001, which is hereby incorporated herein by reference.

FIELD OF THE INVENTION

The invention is related to methods for making and using agents that affect biological compounds, especially agents that contain peptides having sulfonated or sulfated groups. In particular, combinatorial chemistry methods and applications that involve such agents are described, especially agents that bind to heparin-binding sites of proteins.

BACKGROUND

Heparin is a naturally occurring biomolecule that is used for many medical applications. One application takes advantage of heparin's binding to the biomolecule antithrombin III (AT III). Heparin is introduced into a patient's blood, where it binds ATIII and thereby helps prevent unwanted blood clotting. Heparin binds to AT III by interacting with specific heparin-binding sites on ATIII. Heparin's negatively charged sulfate and sulfonate groups play an important role in this binding.

Many biomolecules have heparin-binding sites but heparin binds them only weakly or with little specificity. Without specificity for a target, heparin given to a patient is taken up by other biomolecules and prevented from reaching its target. And if it does reach its target, a weak bind may cause it to have little effect. Heparin, in fact, has many limitations concerning the specificity, speed, and strength of its interactions with other molecules.

Combinatorial chemistry is a technology that involves making many chemicals and screening them. The screening test is used to test the chemicals to determine which ones have a useful chemical property with regards to a given target. Combinatorial chemistry has been successfully used to make many drugs.

SUMMARY OF THE INVENTION

The invention provides systems and methods for making ligands, especially ligands that mimic some functions of heparin and improve on the function of heparin in some circumstances. The ligands have sulfonated or sulfated chemical groups, and sulfated or sulfonated amino acids are preferred. Systems for making heparinic compounds include embodiments using combinatorial chemistry processes that incorporate sulfonated or sulfated amino acids.

An advantage of using ligands of the invention is that they can be tailored to a given application. For example, a ligand that mimics heparin but degrades faster or slower than heparin may be made. Or it may be desirable to target a small subset of heparin-binding protein by tailoring a ligand to bind only to the targeted subset. The systems and methods for making a ligand that mimics a heparinic compound advantageously allow for rapid production of ligands that are targeted to a specific heparin-binding protein.

An embodiment of the invention is a ligand for binding a target biomolecule, the ligand having a peptide with at least one sulf(on)ated amino acid, with the ligand having a specific binding for the target biomolecule. The specific binding preferably has a $K_D$ of less than about 600 μM in physiological solution. The peptide preferably also has at least one positively or neutrally charged amino acid. The target biomolecule preferably has at least one heparin binding site. Another embodiment of the invention is a method for reacting a heparin-binding biological molecule with a ligand, the method comprising exposing the ligand to the target, wherein the ligand has at least one sulf(on)ated amino acid and a $K_D$ for the target biomolecule of less than about 600 μM in physiological solution.

Another embodiment of the invention is a method for generating a ligand that interacts with a heparin-binding target, the method involving providing a target comprising a heparin-binding site, providing a set having members that each comprise a peptide having at least one amino acid that is sulf(on)ated, screening the set with the target to identify at least one member of the set that binds the target, and identifying the ligand by determining a chemical identity for the at least one member of the set that binds the target. The peptide preferably also has at least one positively or neutrally charged amino acid.

Other embodiments of the invention include a ligand for a target having a sulf(on)ated peptide that includes a sequence chosen from the group consisting of derivitized SEQ ID NO: 1–10 and 13–17, and sequences having conservative substitutions thereof, wherein the derivitization is sulf(on)ation of the tyrosines in the sequences. Another embodiment is a ligand for a target, the ligand having a sulf(on)ated peptide that includes a sequence chosen from the group consisting of derivitized SEQ ID NO: 11, 12, and 17–24, and sequences having conservative substitutions thereof, wherein the derivitization is sulf(on)ation of the serines in the sequences. The peptides preferably also have at least one neutrally or positively charged amino acid.

BRIEF DESCRIPTION OF THE FIGURES

FIG. 2 lists some heparinic binding sites that are suitable targets for ligands of certain embodiments of the invention.

FIG. 6 depicts the Sequences reported herein by SEQ ID NO:.

DETAILED DESCRIPTION

Figure 1A:
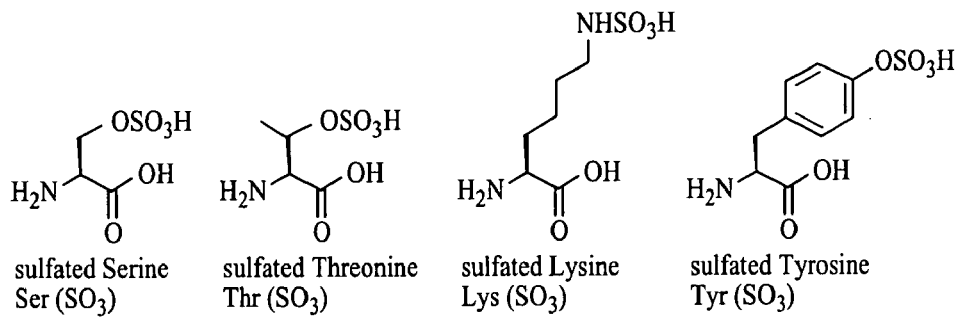
FIG. 1A depicts examples of sulfated amino acids.
Figure 1B:
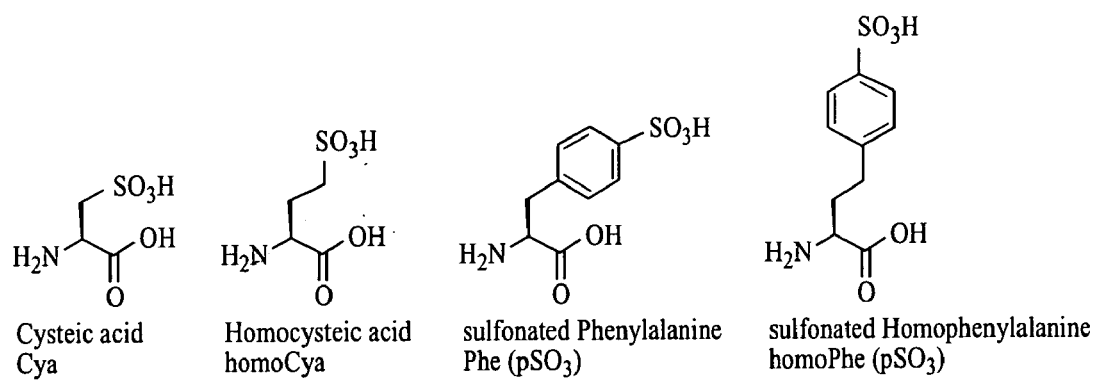
FIG. 1B depicts examples of sulfonated amino acids.
Figure 1C:
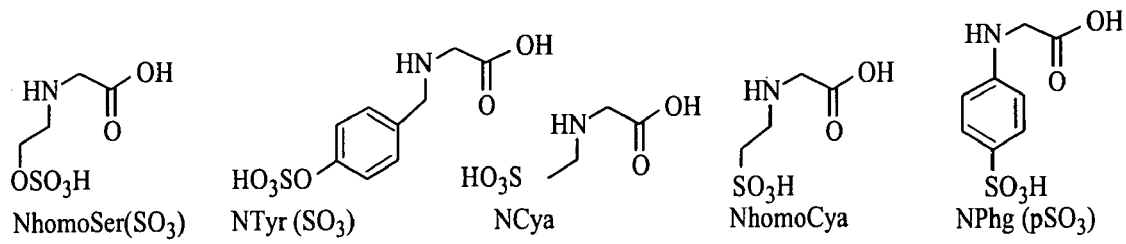
FIG. 1C depicts examples of sulfated and sulfonated amino acids.

Heparin's usefulness stems in part from the variety of ways in which it binds other molecules and the variety of molecules that it binds. Heparin's negatively charged sulfate and sulfonate groups help to create bonds with positively charged groups on other molecules. These bonds are typically involve electrostatic interactions. Other interactions may be important including those driven by hydophilicity, hydrophobicity, and conformational effects. The charge to charge interaction between charged molecules is referred to as an electrostatic interaction and may involve binding or repulsive forces. A binding agent is referred to as a ligand.

The molecule that a ligand binds is referred to as a target. Many biological processes are performed by a ligand-to-target binding event. The binding event can have a variety of effects, including blocking other molecules from binding the target, causing the target to be activated so it performs a new function, or deactivating the target so it becomes inactive.

Many drugs are ligands. Some drugs are agonists that activate their target. Other drugs are antagonists that bind their target and prevent other biomolecules from interacting with the target. Other drugs are affinity binding agents that bind to a target and anchor the target to a support. Heparin is used as a drug that binds to antithrombin III and thereby causes the antithrombin III to deactivate thrombin. Thrombin helps blood to clot so its deactivation by the administration of heparin causes the patient to be less susceptible to blood clots. All of these ligand-target binding events are mediated by electrostatic interactions.

Electrostatic interactions are usually important in biological binding and are often useful for making bioactive agents as markers, agonists, antagonists and affinity binding agents. Sulfates and sulfonates mediate some binding events. They are negatively charged and electrostaticly interact with positive charges on biological molecules. Their hydrophilicity or hydrophobicity and conformation may also participate in the binding event.

In nature, the most common biological molecules that have sulfates and sulfonates are saccharide-like structures, for example, heparin, heparin sulfate and chondroitin sulfate. Nature employs sulfates on proteins to a much lesser extent: sulfation of amino acids is a rare, although important, post-translational modification. A cell makes proteins by joining amino acids into chains. The amino acid is thus a monomer and the chain is a polymer. A peptide has at least two amino acids, and the amino acids may be contiguous or separated. A peptide of amino acids may be described at least in part by describing its sequence. A post-translation modification is generally a change to the amino acid polymer that occurs after a cell polymerizes the amino acids into a polymer. Amino acids that have been reacted to form a portion of a polypeptide are referred to herein as amino acids. For example, amino acids joined to other amino acids via peptide bonds are referred to as amino acids even though some aspects of their structure are thereby changed.

Peptides incorporating sulfated and/or sulfonated amino acids can be highly charged molecules and therefore typically exhibit strong binding to a number of biological entities having appropriate corresponding structure. Peptides, therefore, that have sulfated and/or sulfonated groups are useful, for example, for binding a variety of targets. The preferred targets are those that bind heparin. These targets have heparin binding domains. Binding, as used in the biological sciences, means specific binding. Specific binding generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions. An advantage of a sulfate or sulfonate compared to a carboxylic acid is that the carboxylic acid usually has less specificity for a heparin-binding site.

Approaches by other researchers towards making heparin mimics have been directed towards the use of polysaccharides. Polysaccharides are sugars. These other researchers have used a polysaccharide to mimic a polysaccharide. Especially successful mimics are found in a class of medications referred to as pentasaccharides. Further, some of these researchers have used sulfonated polysaccharides. Some researchers have used dextrans, which are polysaccharides (de Raucourt et al. (1998)). Examples and reviews of the use of polysaccharides as heparin mimics are described in, for example: Herbert et al. (1998), Herbert et al. (1996), Logeart-Avamoglou and Jozefonvicz (1998), Feret (2001), van Boeckel and Petitou (1993), Folkman et al. (1989), Zugmaier et al. (1992), and Parish et al. (1999).

Other researchers have reported various heparin mimics. One example is an engineering polymers that has sulfonic acid groups (e.g., Liekens et al., 1999). This group of polymers was directed against fibroblast growth factor-2 (FGF-2). Engineering polymers lack the advantages of using ligands that incorporate an amino acid, including the suitability of peptides for combinatorial synthesis. Further, peptides have generally superior degradation and clearance properties than engineering polymers. Sulfated peptides directed to biomolecules have been described, e.g., Muramatsu et al. (1997). Muramatsu and colleagues described a sulfated decapeptide directed to the anion-binding exosite of thrombin, a site that is distance from the heparin-binding domain of thrombin. Muramatsu et al. did not describe the use of a combinatorial chemistry approach using peptides to develop their ligand for thrombin. Bentolila et al. (1999) described a poly(N-acryl amino acid) polymer, including certain polymers with sulfated hydroxyprolines. Bentolila, however, describes that all polymers active as heparin mimics had a negative charge density of at least one per amino acid residue. In contrast, embodiments that describe ligands that are effective heparin mimics that have a charge density less than one per amino acid residue are reported herein. Miao et al. (1997) reported a nonsulfated polyanionic compound directed against FGF-2. Combinatorial synthesis with polysaccharides is described, for example, in Patent Application No. WO9926956.

In contrast, this applications describes methods and compositions do not use polysaccharides to mimic heparin. Certain embodiments use combinatorial libraries of sulfated and/or sulfonated amino acids to produce peptides for interacting with biomolecules. Nature uses sulfated amino acids in biological recognition; however, it almost always uses single or isolated sulfate sites. The Examples demonstrate that ligands having specific, very high affinity interactions with suitable targets can be obtained by designing libraries having multiple sulfations or sulfonation sites. Preferably, the libraries have members having sulfated and/or sulfonated amino acids in combination with hydrophobic amino acids. Preferably, the libraries also have amino acids with hydrophobic and/or acid and/or alcohol functionalities. The use of amino acids has many advantages, including the ability to use robust high throughput methods for creating high purity peptides.

Sulfated and sulfonated peptides synthesized by a combinatorial library approach are preferable for making peptides that bind suitable targets. A combinatorial library of peptides is a set of peptides. Every peptide in the library may be unique or some peptides may be duplicative of each other. The library can be tested against a target to determine which members of the library interact most favorably with the target. Thus, ligands that interact with the target molecule, e.g., by binding, are identified and thereby generated. Then the ligands may be mass-produced using commonly known methods. A ligand is the molecule that binds to the target. The target typically has a portion termed a binding site or a binding domain that is most active in the interaction with the ligand. A method of production involving a combinatorial library is preferable because the library size, compound size, and composition can be readily manipulated to obtain molecules with different chemical and biological properties.

Embodiments that are systems and methods for producing ligands that bind to heparin-binding domains are described herein. Certain embodiments of the use of these systems and methods are set forth in the Examples. The systems and methods of the invention, however, are not limited to the Examples. Further, specific ligands and targets are contemplated and set forth herein, e.g., FIGS. 1 and 2. Methods of making and using the systems and methods of the invention are set forth, including suitable ligands, targets such as biomolecules and heparin-binding site motifs, and combinatorial procedures.

Ligands for Interaction with Target Molecules

Preferred ligands include sulfated and/or sulfonated groups disposed on an amino acid. The term sulf(on)ated, as used herein, refers to a chemical group that is either sulfated, sulfonated, or both. This a sulf(on)ated amino acid or peptide is an amino acid or peptide that is sulfated, sulfonated, or both sulfated and sulfonated. Sulfated and sulfonated groups are interchangeable in most circumstances in terms of their binding activity. The sulf(on)ated peptide is preferably Tyr, Ser, Thr, or Lys (FIG. 1A). Other sulf(on) ated peptides may be used, see for example, FIGS. 1A–1C. Standard one and three letter abbreviations for amino acids are used (e.g., Tyr or Y for tyrosine). These abbreviations are included in Alberts et al., *Molecular Biology of the Cell*, 2nd ed., which is incorporated herein by reference for all purposes. X or XXX stands for any amino acid, as appropriate in the context.

As described in Stryer, *Biochemistry*, 3rd ed., hydrophobic amino acids are: Gly, Ala, Val, Leu, Ile, Phe, Tyr, and Trp, and synthetic amino acids that are similar to them with regards to their solubility in aqueous solution. A conservative amino acid substitution is a substitution wherein a hydrophobic amino acid is substituted for another hydrophobic amino acid, and similarly, wherein hydrophilic is substituted for hydrophilic, basic is substituted for basic, or acidic is substituted for acidic. Moreover, substitution of a sulfate for a sulfonate, and vice versa, is a conservative substitution.

Any amino acid that may be sulfated before or after polymerization into a peptide may be used. These include the 20 naturally occurring amino acids as well as synthetic amino acids and modified versions thereof. Peptidic libraries are preferably generated from natural amino acids including those with sulfate functionality. The Examples, below, set forth library syntheses performed using sulfated tyrosine (Tyr($SO_3$)), sulfated serine (Ser($SO_3$)) and sulfated lysine (Lys ($SO_3$)). Certain sulfated and sulfonated peptides are commercially available and may be obtained from commercially known sources, for example BACHEM. Further, the preparation of sulfated amino acids is described in the literature, for example, in Campos et al. (2002).

The ligands are preferably peptides. The peptides or ligands, however, may be associated with a larger structure. The association is useful for delivering the ligands or modifying the uses. Examples of such association include covalent and non=-covalent bonds. Such a structure may be referred to as, for example, a ligand-bearing structure. The larger structure is any biocompatible structure, for example a synthetic polymer, protein, glycosaminoglycan, proteoglycan, natural or synthetic biomolecule, medical device, and an implantable medical device. As further examples, such structures include liposomes, capsules, gels, hydrogels, hydrophobic polymers, hydrophilic polymers, polyethylene oxide, medical device surfaces, catheters, hip implants, stents, vascular grafts, tissue engineering matrices, pacemakers, defibrillators, leads or wires for implantable devices. Further, the ligands may include multiple amino acids that perform the binding function of the ligand. For example, two amino acids on a ligand may be separated by a short non-amino acid spacer, e.g., a synthetic polymer. Examples of polymers are described in the *Polymer Handbook*, 4th Edition, by J. Brandrup, E. H. Immergut, E. A. Grulke, Akihiro Abe, and D. Bloch (Eds.), which is hereby incorporated herein by reference. The ligands are used as part of larger structures in order to impart desirable additional properties to the ligands. The term ligand is used broadly and may include not only those portions chemical moieties that directly participate in a binding event but also a molecule that has a binding moiety.

The ligands are preferably small in size, nontoxic, and not do not elicit an immune response after injection into a patient. Ligands may generally be any size, but a preferred size for a small molecule ligand is less than about 5000 Da. A more preferred size is less than about 2500 Da. Peptidic ligands of various sizes can be quickly generated using the methods described herein. Tetrapeptides and decapeptides are described in the Examples, but the appropriate length of the peptides may be tailored to each application. Small ligands typically are advantageous because they may be more readily introduced into the cells of a patient. Ligands that have lipophilic, aromatic, or heterocyclic structures that allow them to cross cell membranes and the blood-brain barrier are usually preferable.

An advantage of adding neutral or charged amino acids to a ligand is that the solubility and overall charge of the ligand is thereby affected. Solubility has an important effect on the processing and manufacture of the ligands since the choice of commercial solvents is not unlimited and some solvents are more safe or less expensive to use than others. The overall charge of the peptide and/or ligand also affects the ability of a cell to uptake the ligand, a process that is important when targets are within cells. The glycocalyx of most cells is highly negatively charged so that the presence of neutral or positive charges may enhance uptake in some cases. Moreover, a ligand with a high positive or negative charge may tend to exhibit unwanted nonspecific binding, for example, after injection into a patient.

An advantage of using sulfated (but not sulfonated) peptides is that sulfated peptides gradually desulfate in vivo and thereby gradually lose their strong binding affinity, which can be useful in delivery systems as well as in clearance from the body. Further, sulfated peptides may be desulfated by chemical means and easily evaluated by standard sequencing techniques, a further advantage of sulfated peptides. On the other hand, an advantage of sulfonated ligands is that the sulfonated groups are more stable than sulfated groups, a feature that is useful in some circumstances.

Ligands that incorporate synthetic peptides or non-peptides are also contemplated. Synthetic means that which is not found in nature. Examples include peptoids (Simon et al., 1992), oligocarbamate (Cho et al., 1993), oligoureas (Burgess et al., 1995), vinylogous sulfonyl peptides (Gennari et al., 1995), peptidosulfonamides (de Bont et al., 1996), azatides (Han and Janda, 1996), ketides (Khosla and Zawada, 1996), and sulfated peptides (Muramatsu et al., 1997). Further, ligands may be rigid, flexible, linear, branched, dendritic, cyclized, or exhibit specific physical, chemical, or structural properties that are more favorable therapeutically. Natural amino acids are preferable but D-amino acids and other synthetic amino acids, especially those with sulfonate or other functionality can be used. The peptides described in the Examples have an amide ($CONH_2$) terminus. Other termini may be substituted, including ends for cyclization.

It is also possible, when desirable, to target a small subset of heparin-binding proteins by tailoring a ligand to bind only to the targeted subset. Targeting may be achieved by screening ligands, as described herein, against targets in the presence of molecules that compete with the ligand or that are not supposed to bind the ligand. For example, a peptidic ligand directed against Antithrombin III (ATIII) may be screened in the presence of heparin so that the ligand will bind to ATIII more strongly than heparin does (see Examples). Alternatively, a set of ligands for the target could be generated and the ligands could be screened by determining their fate in the system where they will be used. For example, a peptidic ligand against ATIII could be marked and injected into an animal or a human patient. The marker could be used to determine which ligands most effectively bind ATIII as opposed to other substrates.

The synthesis of peptides is performed according to protocols known to those skilled in these arts. Solid phase synthesis typically involves reacting a solid surface, typically a bead, with a first amino acid. Subsequent amino acids are reacted with the first amino acid to build a peptide. The reaction processes often require that some functional groups on amino acids be protected with protecting groups. The protecting groups are added and removed as needed. The synthesis of peptidic libraries is described in the literature, for example, in Thompson and Ellman (1996). Synthesis involving combinatorial biocatalysis is described, for example, in Khosla and Zawada (1996) and Khmelnitsky (1996).

Target Molecules for Interaction with Ligands

Suitable target molecules are biomolecules, particularly biomolecules that have a heparin-binding domain or that bind to heparin or heparan sulfate. Ligands may be made for any heparin binding domain according to the production methods described herein. Moreover, the ligands can be made with a desired degree of specificity and/or binding strength for the target molecule. One method for achieving these properties is to screen libraries of peptides for the desired properties. Target molecules include, but not limited to, peptides, proteins, glycoproteins, polysaccharides, antibodies, enzymes, and receptors on or in virus particles, bacteria, fungi, and cells. Embodiments of the method of producing ligands for target molecules are set forth in the Examples, below, with the targets being growth factor vascular endothelial cell growth factor (VEGF) and ATIII.

ATIII is an example of a suitable target. The term ATIII refers to all variations, mutants, derivatives, and isoforms of human antithrombin III. ATIII is a serine protease inhibitor in the serpin family that plays an important role in the intrinsic blood coagulation. When heparin binds ATIII, the ATIII changes its shape and becomes activated. Activated ATIII is able to inhibit factor Xa or thrombin. Inhibition of one of these factors in blood causes the blood to have less clotting activity. Only a pentasaccharide unit structure of heparin is necessary for binding of the antithrombin III to cause inhibition of factor Xa. However, a much longer part of heparin must bind to antithrombin III to cause the inhibition of thrombin.

Antithrombotic drugs are useful for many clinical applications. Since ATIII is normally present in the blood, drugs that cause it to become activated would be useful. The only reported heparin mimetics have apparently been based on saccharides, e.g. synthetic sulfated pentasaccharide or polymers, e.g. dextran sulfate or sulfonated polystyrene. However, the present application describes systems and methods for making sulfated peptides that bind to the heparin binding domains of targets such as ATIII. Further, the present application describes specific peptide based ligands that use sulfated amino acids to bind the heparin-binding domain of ATIII.

VEGF, basic fibroblast growth factor (bFGF), and platelet-derived growth factor (PDGF) are also examples of suitable targets. Angiogenesis, the formation of new blood vessels from existing ones, is involved in wound healing as well as the pathogenesis of a variety of diseases including proliferative retinopathies, rheumatoid arthritis, and cancer. The process is controlled by a number of growth factors such as VEGF, bFGF, and PDGF. Each of these growth factors have a biological activity that can be potentiated or inhibited by binding to the sulfated polysaccharide, heparin. Molecules that mimic heparin by binding to these proteins and modulating activity are useful. Such heparin mimics are preferably small, well-defined, specific, and nontoxic.

Growth factors are suitable targets, including the fibroblast growth factor family, heparin-binding epidermal growth factor, the vascular endothelial growth factor family, the transforming growth factor beta superfamily, insulin-like growth factor, bone morhpogenetic proteins (BMPs), hepatocyte growth factor (HGF), leiotrophin, nerve growth factors, and neurite growth promoting factor-1 (NEGF1). Other suitable targets are extracellular matrix molecules, for example fibrin(ogen), laminin, and fibronectin. Components of the blood system, including the intrinsic and extrinsic cascade are suitable targets. Cell surface receptors that bind heparin are suitable targets, for example integrins, cell adhesion molecules, and cell-cell adhesion molecules. Other suitable targets are proteases and protease inhibitors, including heparin, heparinase, and heparinase.

Heparin mimics can be used to modulate the angiogenic activity of heparin-binding growth factors. Heparin itself has been employed towards this end, but the variable activity of different preparations due to their heterogeneous composition, toxicity due to its anticoagulant activity, and low affinity ($K_D$ of about 5.5 µM) are drawbacks to using the polysaccharide. These drawbacks have led to the study of other natural and synthetic molecules that mimic heparin. However, many such mimics demonstrate high toxicity and low therapeutic indices, are nonspecific, or give inconsistent results. For example, sugars such as pentosan polysulfate (PPS), sulfated polysaccharides other than heparin, and cyclodextrins can be used as heparin substitutes but demonstrate similar problems as heparin. The sulfated compound suramin and analogs also inhibit growth factor induced angiogenesis. However these compounds in many circumstances are not specific, exhibit serious toxicity, and have low therapeutic indices.

The design, synthesis, and implementation of methods and combinations for producing sulfated peptides that bind with high affinity to the heparin-binding domain of VEGF is described in the Examples. VEGF initiates angiogenesis by activating receptors that stimulate vascular endothelial cell (EC) proliferation and migration. Unlike other angiogenic growth factors, such as bFGF, VEGF activity is highly specific to endothelial cells. VEGF is characterized as a heparin binding growth factor. Heparin found on cell-surfaces as heparin sulfate proteoglycans (HSPGs), is apparently necessary for the growth factor-induced angiogenic activity to occur. There is much evidence suggesting that cell-surface HSPGs stabilize VEGF binding to its receptors, thereby stimulating angiogenic activity. Consistent with this, depending on heparin size and concentration, exogenous heparins potentiate or inhibit VEGF binding to its cell-surface receptors. Thus sulfated or sulfonated ligands, especially peptidic ligands that mimic heparin, can be used to modulate VEGF activity. Additionally, such ligands are useful for bind and release applications.

Suitable target molecules often contain heparin binding sites. Many such sites are known as described in, for example, Fromm et al., 1997. FIG. 2 sets forth some of the known sites. A heparin binding site is a biological term that includes molecules that bind heparin as well as natural variants of heparin, for example, heparan.

Dissociation Constants Between Ligands and Binding Sites

Ligands are often competing with other ligands for a binding site in a physiological setting. Ligands bind the binding site but periodically become detached. The time that the ligands spend attached to the binding site is long if the ligand has a high binding affinity for the site. The dissociation constant, Kd, is a quantitative measure of the binding affinity of a ligand for a particular binding site. For a reaction of T+L⇌TL where L is the concentration of ligand, T is the concentration of the Target that the ligand binds and TL is the complex formed by the ligand and target, the Kd is calculated by dividing the product of the concentrations of the reactants by the concentration of the product: Kd=[T][L]/[TL]. The dissociation constant Kd is typically reported at the concentration where [TL]/([TL]+[T])=0.5, and is represented as $K_D$, also referred to herein as the half-saturation dissociation constant. Thus $K_D$ represents the concentration of ligand required to saturate exactly half of the binding sites available on T. A high value of $K_D$ represents a weak binding affinity but a low value of $K_D$ represents a strong binding affinity between the target and the ligand.

The customary method for calculating dissociation constants involves using the slope of a line on a Scatchard plot generated for multiple concentrations. This process and variations of this process are known to those skilled in these arts, for example to accommodate multiple ligands or multiple binding sites on a target.

In the present application, the dissociation constants are measured in a solution that reflects physiological solutions with an osmolarity of approximately 300–330 mOsmolar and a pH of between 7.0 and 7.4. Ligands preferably have a $K_D$ of less than about 600 μM for the target. More preferably the $K_D$ is less than about 60 μM, even more preferably less than about 6 μM, yet more preferably less than about 0.6 μM, and furthermore even more preferably less than about 0.06 μM.

Combinatorial Chemistry

There are at least five common techniques for performing combinatorial library production that are applicable to the production of the ligands, see Lam (1997), see also Al-Obeidi et al. (1998), see U.S. Pat. Nos. 5,424,186; 5,449,754; 5,503,805; 5,650,489; 5,962,736; 6,042,789; 6,051,439; 6,083,682; 6,117,397; 6,168,913; 6,168,914; and 6,355,490. The common techniques are biological libraries, spatially addressable parallel or solid phase solution libraries, synthetic library methods requiring deconvolution, a one-bead, one-compound method, and synthetic library methods using affinity chromatography selection. In general, combinatorial library production techniques involve: generating a set of peptides (also referred to as a library) from amino acids, typically using a random or semi-random algorithm to arrange the sequences of the peptides; rapidly screening the set for a specific biological property, typically by determining which peptides bind to a target; and identifying the peptides that have the biological property. Identification of the peptides is typically performed by a deconvolution method, by direct chemical analysis, or by analysis of the amino acid sequence.

The general types of combinatorial production methods for the ligands have various embodiments. Spatially addressable parallel solid phase or solution phase libraries include, for example, multi-pin technology, SPOTs-membrane, light-directed peptide synthesis on chips, and diversomer technology. Synthetic libraries requiring deconvolution include an iterative approach, positional scanning, recursive deconvolution, and orthogonal partition approaches.

Combinatorial libraries of peptides were limited to a few hundred compounds when first introduced, e.g., in about 1984. But the preparation and screening of many millions of peptides is presently feasible, especially when using the biological approach (e.g., Devlin et al., 1990), an iterative approach to solution phase peptide libraries (e.g., Houghton et al., 1991), a one-bead one-compound approach (e.g., Lam et al., 1991), or a split-pool iterative approach.

The biological library involves the use of cells, phages, plasmids, and/or polysomes to generate peptides. The phage approach is exemplified by Parmley and Smith, 1988. The plasmid approach is exemplified by Schatz, 1993. The polysomes approach is exemplified by Kawasaki, 1991. The biological approach is particularly useful when large ligands or biological compounds that bear ligands are desired.

Spatially addressable parallel solid or solution phase libraries are made by synthesizing peptides on a solid phase support so that the peptides can be spatially addressed and the sequence of each of the peptides is known or the sequences are predetermined. Typically, the sequence of each peptide is predetermined so that the sequence of the peptide is ascertained merely by determining its position. The multi-pin approach is exemplified by Geysen et al, (1984). The SPOTS membrane approach is exemplified by Frank (1992). The light-directed peptide synthesis on chips approach is exemplified by Fodor et al. (1991). The diversomer approach is exemplified by DeWitt et al. (1993).

Synthetic libraries requiring deconvolution include an iterative technique. The iterative technique is exemplified by Blondelle et al. (1995). This technique involves multiple peptide synthesis, screening, and analysis steps. For example, for a procedure using 20 amino acids and a ligand of ten amino acids in length, multiple peptide mixtures are made that have the first position and the second position of the ligand as a known, with every possible combination of the two peptides being present. The remaining positions are random amino acids. Thus every combination of two known peptides in the first two positions results in a total of 400 mixtures. The multiple mixtures are screened for biological activity and the most active mixture is selected. A new set of mixtures is made that has the first two positions fixed and the third position systematically varied. Thus 20 new mixtures are made that have each of the first three positions as knowns. The mixtures are then screened for a biological property and the process is repeated.

A related deconvolution method is the positional scanning method exemplified by Dooley and Houghten (1993). As an example for a hexapeptide ligand and 20 amino acids, 120 mixtures are made with each mixture having a known amino acid in one of the six positions. The mixtures are screened and the mixtures that are active can be used to assemble the ligand.

Figure 3:
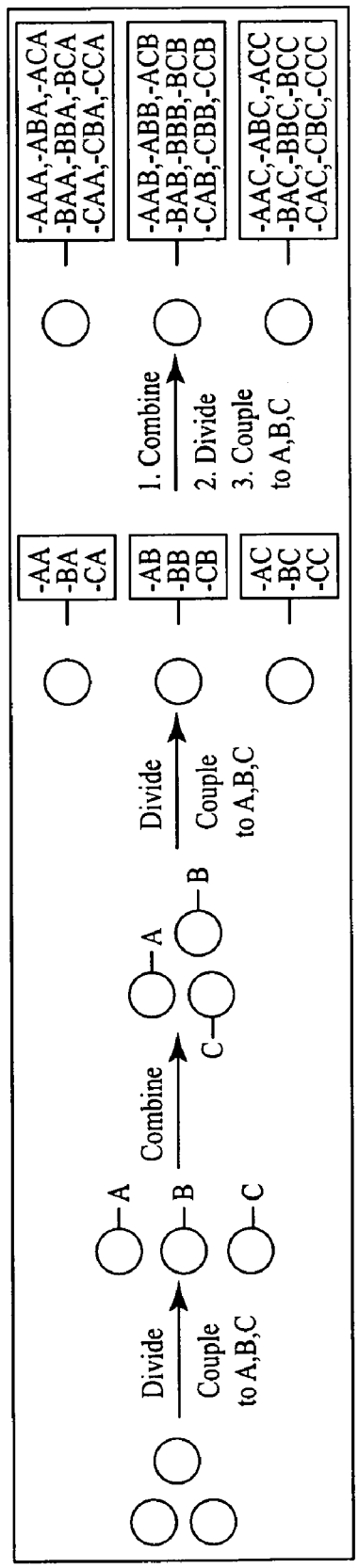
FIG. 3 depicts a scheme for performing combinatorial chemistry.

Another related iterative technique is the split synthesis technique, exemplified by Erb et al. (1994). FIG. 3 depicts the algorithm for this approach, with the peptides being synthesized by solid-phase synthesis wherein beads are prepared with an amino acid attached and peptides are built up by sequentially binding additional amino acids. Referring to FIG. 3, mixtures are made that have a plurality of beads that each have a known amino acid A, B, or C. The beads are combined into one mixture and then divided into three identical mixtures (since there are three known amino acids). Each mixture has a known amino acid A, B, or C attached to make every possible combination of amino acid dimers that can be made with A, B, and C. The mixtures are then combined and divided into nine identical mixtures (since there are nine different combinations of dimers). Each mixture is reacted with A, B, C, combined, and divided into 27 identical mixtures. The process is repeated as needed to achieve the desired length. Referring to FIG. 3, each bead ultimately bears an individual, unique peptide. A single screening step is preferably performed after all combinations have been made.

Another related iterative technique for making the ligands is the orthogonal partition technique, exemplified by Deprez et al (1995) and Pirrung and Chen (1995). This technique combines the split synthesis and positional scanning approach.

Figure 4:
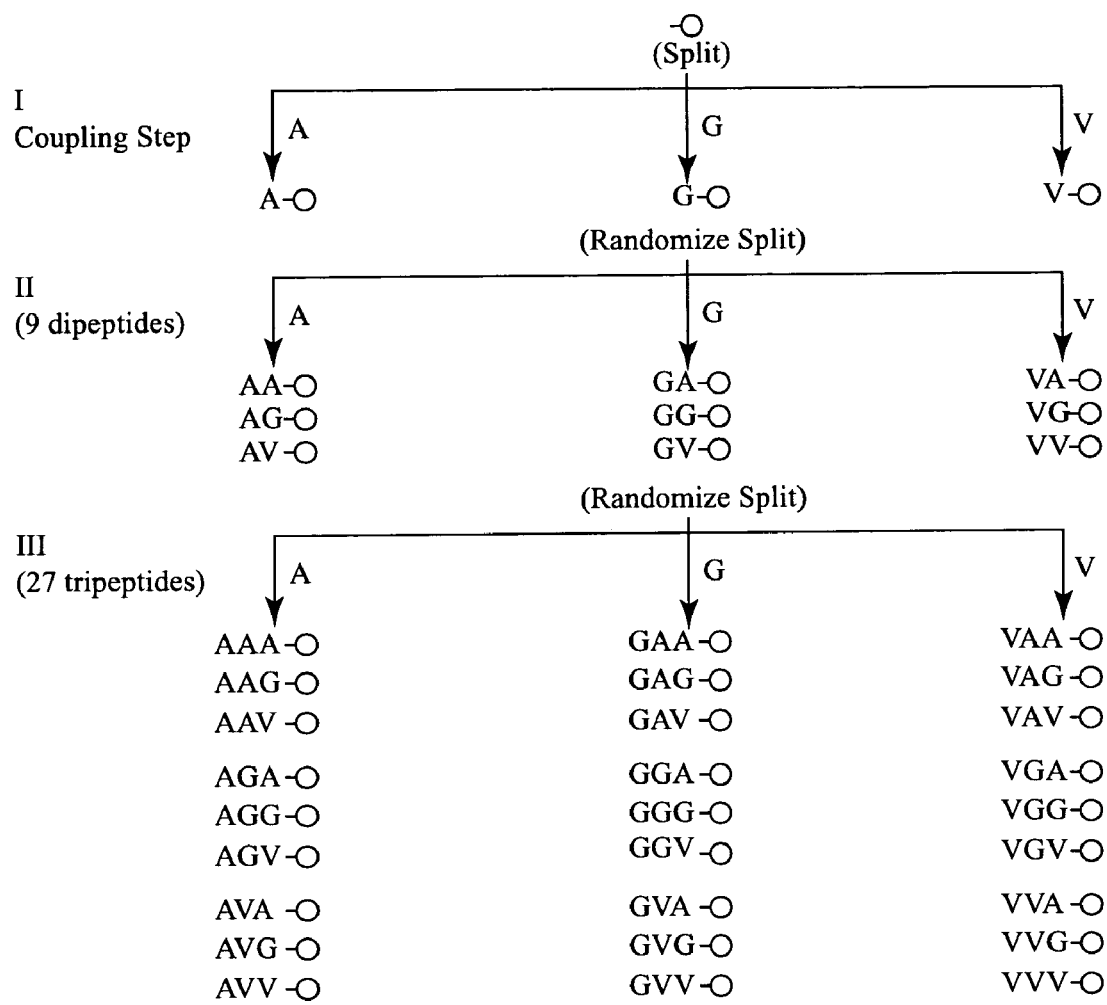
FIG. 4 depicts an alternative combinatorial chemistry scheme.

Another related iterative technique for making the ligands is the one-bead one-compound technique, as is described by Lam and Lebl (1996) and Lam et al. (1997). A particularly effective approach of this technique uses the split synthesis method. Referring to FIG. 4, beads, represented by "O" are covered with a single amino acid. The beads are split into groups and each bead is then reacted with every amino acid that is to be used. The groups are comibined, split, and reacted with an additional amino acid. In the case of 20 amino acids, the beads are initially in 20 groups and each bead receives a unique amino acid. The resins are then mixed, deprotected, and portioned into 20 groups. Each group receives an additional amino acid. A pentapeptide library with 20 amino acids in each coupling cycle has $20^5$ (3.2 million) permutations. Such a library can be rapidly generated in a modest apparatus in a university setting in 2–3 days, see Lam, 1997. Typical commercial settings could produce such a library much more rapidly.

A synthetic library method using affinity chromatography selection is also useful for producing the ligands. This method typically involves generating a library in solid phase, usually by a split synthesis method using beads. The peptides are removed from the beads and into solution with the peptides present in equimolar amounts. The solution is then passed through an affinity chromatography column bearing an immobilized target molecule. After appropriate washing steps, the peptides are eluted from the column and sequenced to determine which peptides bind the target. There are many variations of this technique, for example, the bound peptides may be eluted using successive washes of increasing strength so that peptides of different binding affinities are captured in different elution fractions. Exemplary reports of this technique are in Songyang et al. (1993 and 1995).

Some of the combinatorial methods require a step of determining the structure of biologically active ligand, for example the one bead—one compound method. Automatic sequencing by Edman degradation is preferable since this process presently has a detection sensitivity of better than 1 pmol. Alternative approaches, however, include mass spectroscopy, e.g., matrix-assisted laser desorption ionization mass spectroscopy (MALDI), ionization mass spectroscopy, or MS-MS techniques, and the use of tags, especially chemical tags.

A multiplicity of screening strategies is available. One approach is the use of a solid phase assay. The ligands are attached to a solid support, e.g., a chip, pin, bead, plastic sheet, glass, filamentous phage. The target is added to the support and the ligands are examined for biological activity. Such activity may include for example, binding, or a functional assay such as proteolysis or phosphorylation. Binding is conveniently measured directly, (e.g., by visualization of a dye on the target) or indirectly (e.g., by a reporter groups such as an enzyme).

Another screening method involves solution phase assays. The ligands are in a solution that is exposed to the target. The interaction between the ligand and the target is detected and the ligand is isolated. Examples of such techniques include competitive receptor binding assays with a known radiolabeled target or ligand, competitive ELISA assay using plate-coated antigens, enzymatic assays such as proteolytic assay using a fluorgenic substrate, anti-bacterial assays, and cell-based signal transduction assays.

Split-pool and iterative deconvolution combinatorial synthesis approaches are preferred for making ligands that have sulfated amino acids; however, other techniques may also be applied, including positional scanning, array synthesis, non-linear, double, and orthogonal strategies. The libraries are preferably screened on solid supports, but may be readily screened by other techniques, for example, in solution or using the multipin method.

Combinatorial chemistry is a preferred embodiment of the method for producing ligands. Other techniques, however, are suitable. Peptidometics based on sulfated and sulfonated amino peptides can also be either discovered directly and/or by rational design.

Uses and Application

Ligands that are sulfated or sulfonated can be produced for targets that have heparin-binding domains. The ligands are useful for many applications, including those that require a step of binding the target. These applications include both in vitro and in vivo work. Examples of such applications for these ligands include uses as agonists, antagonists, affinity binding agents, markers, and delivery vehicles. An example of an agonist is a ligand that binds its target and thereby mimics the effect that some other ligand would have elicited from the target. Another example of an agonist is a peptide that acts as a heparin mimic that binds to ATIII and induces a conformational change to the protein in a similar manner to that done by heparin, thus inducing the thrombin-inhibiting activity of the ATIII. The ligands are useful in biotechnology and medicine, for example, as markers, agonists, antagonists and specific affinity binding agents.

An example of an antagonist is a ligand that binds to a target and thereby stops or reduces the biological activity of the target. Another example is a peptide that binds to a growth factor via its heparin-binding domain alone or in combination with other sites on the protein, so as to block binding of the growth factor to other molecules. In the case of VEGF, its binding may be blocked to its low affinity or high affinity cell-surface receptors. Binding of the growth factor to cell-surface receptors, especially the low affinity cell surface receptors, involves the heparin affinity binding site, and blocking this site can be used to block VEGF's biological activity.

An example of an affinity binding agent is a ligand that binds to a biomolecule which is then immobilized. When immobilized on a purification support, the affinity between the peptide and, for example, a growth factor, is used to purify the growth factor from complex biological or fermentation mixtures. When immobilized on a drug delivery matrix or implantable device, the growth factor is retained for biological action near the device or is released from the device.

An example of a marker is a ligand that is complexed with an agent so that an interaction between the ligand and a target is marked. Examples include ligands complexed to fluorescent molecules, dyes, avidin, biotin, antibodies, enzymes that are used to create a stain, horseradish peroxidase, and radioactive labels. Other examples include DNA, proteins, green fluorescent protein, radio wave emitters, contrast agents, and nanoparticles.

Biological molecules can serve as targets and be marked. Markers show how the targets are expressed and function. The need for markers is more acute since the completion of the human genome project since many molecules that have been discovered have unknown expression and function. Thus any ligand that binds to a biomolecule is useful as a marker. Markers may be issued in vitro or in vivo. In vitro uses include stains for histology and as visualization tools for a fluorescent microscope. In vivo uses include tagging a target to ascertain its concentration, distribution or movement. For instance, the concentration of a growth factor in the liver and its clearance time can be monitored by injecting the liver with a marker having a ligand for the growth factor. The marker can be detected to determine the fate of the growth factor. Many markers presently used for in vivo use may be adapted for use with a ligand, for example, by adding the ligand to the marker or replacing the marker's ligand with a ligand made as described herein.

Embodiments include ligands that have a half-life controlled by degradation, especially degradation of sulfates. For example, a ligand may have multiple sulfations that interacting with a binding site. Progressive degradation of the ligands results in a ligand having progressively less affinity for the target. Alternatively, the ligand may have a limited number of sulfations and have an activity that drops to essentially background levels when the sulfation is degraded. A limited half-life is useful for controlling release of bound factors. For example, a growth factor bound to a medical device with a ligand could be released by degradation of the ligand. The degradation of a sulfate may be influenced by factors such as steric hindrance, local pH, and folding. Ligands may be designed with these factors so as to control sulfate degradation. Another use of a degradable ligand is to control the half-life of the ligand in the patient. For example, a short half life ligand that inhibits blood clotting could be administered to a patient. The ligand would then degrade and obviate any need to administer an agent that would restore the patient to a normal coagulation state.

Ligands that bind and activate ATIII may be used, for example, to inhibit blood clotting. The ATIII-binding ligands maybe introduced into a patient at the concentration required to achieve the desired level of inhibition. Ligands that bind to VEGF and inhibit its activity may be used, for example, for inhibiting angiogenesis. Thus the ligands may be useful for tumor therapy, treatment of rheumatoid arthritis, diabetic angiopathy, eye disorders such as retinal hyperplasia, and chronic inflammatory disease characterized by hypoxia, or other diseases characterized by uncontrolled angiogenesis.

An example of a delivery vehicle is a ligand used to deliver some other agent to a desired location or a desired target. For example, a ligand complexed with a poison could be used to deliver the poison to the ligand's target, e.g., a pain receptor, T-cell, or cancer cell. Or a ligand could be attached to a liposome so that the liposome would attach to the ligand's target, e.g., a particular cell type.

Thus existing technologies that use ligands to interact with targets may be adapted for use with ligands as described herein. For example, the antibodies used to deliver enzymes as described in U.S. Pat. No. 5,851,527 could be replaced with ligands made as described herein. Or the antibody-based approach used to neutralize growth factors as described in U.S. Pat. No. 5,662,904 could be adapted to use with ligands that are described herein.

Delivery

The ligands may be delivered by suitable means adapted to the application. Examples of delivery of a ligand include via injection, including intravenously, intramuscularly, or subcutaneously, and in a pharmaceutically acceptable solution and sterile vehicles, such as physiological buffers (e.g., saline solution or glucose serum). The ligands may also be administered orally or rectally, when they are combined with pharmaceutically acceptable solid or liquid excipients. Ligands can also be administered externally, for example, in the form of an aerosol with a suitable vehicle suitable for this mode of administration, for example, nasally. Further, delivery through a catheter or other surgical tubing is possible. Alternative routes include tablets, capsules, and the like, nebulizers for liquid formulations, and inhalers for lyophilized or aerosolized ligands.

Many aspects of ligand delivery are described herein. Delivery of a ligand may entail delivery of the ligand itself or delivery of the ligand as well as structures or compounds that the ligands is attached to or associated with.

Presently known methods for delivering molecules in vivo and in vitro, especially small molecules or peptides, may be used for the ligands. Such methods include microspheres, liposomes, other microparticle vehicles or controlled release formulations placed in certain tissues, including blood. Examples of controlled release carriers include semipermeable polymer matrices in the form of shaped articles, e.g., suppositories, or microcapsules. A variety of suitable delivery methods are set forth in, for example, Senel et al. (2001), Cleland (1997), Okada H and Toguchi (1995), Lehr (1994), Jabbal-Gill et al. (2001), Fix (1996), Duncan (1992), Langer and Moses (1991), Sanders (1990) Eppstein (1988), Hyon (2000), Verma et al. (2000), Haroun and Brem (2000), Meers (2001), Brandl (2001), Banerjee (2001), Ravi (2000), Hatefi an Amsden (2002), Vandamme (2002), Lavasanifar et al. (2002), Verma and Krishna (2002), Sood and Panchagnula (2001), Zimmer and Ashburn (2001), Bussemer et al.(2001), Regar et al. (2001), Lo et al. (2001), Qiu et al. (2001), Grabow et al. (2001), Torchilin (2001), Pillai et al. (2001), Vyas et al. (2001), Krafft (2001), Groothuis (2000), Soppimath et al. (2001), Muller (2000), Sinha and Kaur (2000), Kumar (2000), Hussain (2000), Ettenson and Edelman (2000), Chorny et al. (2000), Gonda (2000), Haroun and Brem (2000), and U.S. Pat. Nos. 5,626, 877; 5,891,108; 5,972,027; 6,041,252; 6,071,305; 6,074, 673; 6,083,996; 6,086,582; 6,086,912; 6,110,498; 6,126, 919; 6,132,765; 6,136,295; 6,142,939; 6,235,312; 6,235, 313; 6,245,349; 6,251,079; 6,283,947; 6,283,949; 6,287, 792; 6,296,621; 6,309,370; 6,309,375; 6,309,380; 6,309, 410; 6,317,629; 6,346,272; 6,350,780; 6,379,382; 6,387, 124; 6,387,397 and 6,296,832. Additional methods of delivery are described in copending U.S. patent applications Ser. No. 10/021,508 filed Oct. 22, 2001; Ser. No. 10/035,625 filed Dec. 28, 2001; Ser. No. 09/811,901, filed Mar. 19, 2001; Ser. No. 09/738,961 filed Dec. 15, 2000; Ser. No.

09/772,174 filed Jan. 28, 2001; Ser. No. 09/798,338 filed Mar. 2, 2001; and Ser. No. 09/586,937, entitled "Conjugate addition reactions for the controlled delivery of pharmaceutically active compounds", filed Feb. 6, 2000.

The systems and methods described herein are examples of the invention and are not intended to limit it scope and spirit. Persons skilled in these arts will appreciate variations in the embodiments of the invention after reading this disclosure. All of the publications cited or otherwise referenced herein, including books, journal articles, patent applications, and patents, are hereby incorporated herein by reference.

EXAMPLE 1

Production of Ligands for VEGF Target

Sulfated peptides assembled into a library according to a split-pool synthesis approach were used to produce ligands that bind to VEGF. The synthesis was semi-random, with a portion of the sequences in the library being rationally chosen to make peptides that bind with high affinity to VEGF.

Library Synthesis

Fmoc-Gly-Gly-Gly-Gly-PEGA resin was prepared by standard manual fluorenylmethoxycarbonyl (Fmoc) solid phase peptide synthesis by subjecting amino polyethylene glycol acrylamide (PEGA) resin (3.6 g, 0.22 mmol) to Fmoc-Gly-OH (0.26 g, 0.86 mmol), 1-hydroxybenzotriazole (HOBT, 0.12 g, 0.86 mmol), 2-(1H-benzotriazole-1-yl)-1,1,3,3-tetramethyluronium hexaflurophosphate (HBTU, 0.33 g, 0.86 mmol), and N,N-diisopropylethylamine (DIEA, 0.3 mL, 1.7 mmol) a total of 4 times. The Fmoc-Gly-Gly-Gly-Gly-PEGA resin (0.22 mmol) was then split into 9 equal portions and loaded into 9 wells of a 48 well, fritted plate. The resin was swelled for 1 h with DMF and rinsed with DMF (3×4 mL). The Fmoc groups were then removed using 20% piperidine in DMF (2×4 mL×10 min per well), and the resin was rinsed with DMF (3×4 mL). Into a vial containing HOBT (0.12 g, 0.86 mmol) and HBTU (0.33 mg, 0.86 mmol) was added 18 mL of DMF and the vial was agitated until the solids dissolved. The solution was split into 9 equal portions and added to 9 vials containing 0.096 mmol of Fmoc-Tyr(SO$_3$)—OH, Fmoc-Asp(tBu)-OH, Fmoc-Glu(tBu)-OH, Fmoc-Ser(tBu)-OH, Fmoc-Gly-OH, Fmoc-Ala-OH, Fmoc-Val-OH, Fmoc-Ile-OH, or Fmoc-Phe-OH. The vials were agitated until the solids dissolved before DIEA was added (34 µL, 0.19 mmol per vial). Each vial was added to one portion of resin, the plate was sealed, and mechanically agitated for 1 h. The resin was then rinsed with DMF (5×4 mL), collected, thoroughly mixed, and split into 9 equal portions. The procedure was repeated 3 more times before the resin was pooled, rinsed with DMF (5×4 mL), DCM (5×4 mL), and MeOH (5×4 mL). To remove the protecting groups, 33 mL of TFA:TIS: H$_2$O (95:2.5:2.5) that had been cooled to 4° C. was added to the resin and the mixture was kept at 4° C. for 2 h before removing the solution and washing the resin with cold TFA (20 mL) followed by MeOH (400 mL). The deprotected library containing many copies of about 6,600 different peptides was stored swollen in MeOH at −20° C. until use.

Standard Fmoc, solid-phase manual synthesis of the library was undertaken using HBTU, HOBT, and DIEA in DMF as coupling agents. Poly(ethylene glycol)-based NOVA-biochem amino-PEGA beads were employed due to the low fluorescence background and favorable swelling characteristics of this resin in water. Since the screening process involves identifying beads that have fluorescence, a low background signal is important. Standard TENTAGEL resin gave an inhomogeneous background fluorescence when viewed through fluorescein or Dapi filters. A tetraglycine space was inserted between the anchor of the resin and the carboxyl end of the library to increase accessibility to VEGF during the screening process and to aid in the characterization of the library. The tetraglycine is believed to not specifically bind VEGF since most of the peptides in the library that had tetraglycine lacked specific activity. The protecting groups of the peptides were removed using TFA at 4° C. in order to prevent desulfation of the tyrosine. In this way, many copies of the 6,600 member library were synthesized.

The rational choice of portions of the sequence was based on an examination of the functionality of heparin and the heparin-binding site of VEGF. The rational choice step is optional and was employed for convenience so that the size of the library could be reduced. In this case, the target molecule VEGF was known to have basic amino acids, arginine and lysine, in a putative heparin-binding domain. Since four amino acids is the minimum peptide length that could span the smallest region of this heparin-binding domain, the length of the peptides in the library was set at four. Heparin is known to contain sulfate, carboxylic, and hydroxyl groups. Therefore, a sulfated tyrosine, aspartic acid, glutamic acid, and serine were included as amino acids for the peptides in the library. Further, since hydrophobic interactions were believed to assist in heparin binding, hydrophobic amino acids glycine, alanine, valine, isoleucine, and phenylalanine were also employed. Thus the tetrapeptide library was assembled from nine amino acids to make $9^4$ or about 6,600 compounds. Alternatively, for example, all 20 natural amino acids could have been used to make a library of $20^4$ or about 160,000 compounds.

Library Screening

The beads (about 10 copies of the library) were swelled in H$_2$O for 1 h. The mixture was subjected to centrifugation and the water was removed. The coumerin-VEGF solution in TBS was added (~0.1 mg/mL) to the beads for 1 h before splitting the beads into 6 portions and placing them into a 6-well plate. The beads were then shaken for 16 h at room temperature before the VEGF-coumerin solution was removed. As controls, unsubstituted PEGA resin (10 mg) and heparin agarose (10 mg) were also incubated with the coumerin-VEGF. The beads and controls were then observed through a dissecting microscope equipped with a UV black lamp. The beads and controls were washed TBS until the PEGA control beads were non-fluorescent. The library beads and heparin-agarose beads were then subjected to washes with 20 mM Tris at pH 7.6 containing 0.25 M NaCl (2×), followed by 0.5 M (3×), 1 M (10×), and 2 M (2×) NaCl. While viewing with the dissecting microscope and UV black lamp, a micropipette was utilized to retrieve individual beads (288 in total) that were brighter than the background beads, and each bead was placed into an individual well of a 96 well plate. The plates were then stored at 4° C.

Bead Ranking

The fluorescent signal of each bead was quantified by imaging each individual bead (keeping the gain consistent and white balance set to zero) on an inverted microscope equipped with a Dapi filter. The radius (r) and sum of the pixels (Σ Pix) of each bead was determined after converting each image to grayscale on MATROX INSPECTOR. Using INTERACTIVE DATA LANGUAGE and EXCEL, $\chi^2$ minimizations were performed on the sum of the pixels versus the radius and the best fit was determined to be 2.35 (Appendix 1). Each bead was then ranked according to $\chi$ Pix/r$^{2.35}$ (Appendix 2).

Bead Analysis

In order to facilitate analysis and remove the coumerin-VEGF, the Tyr(SO$_3$) residues were desulfated. The beads were washed with H$_2$O (1×0.2 mL) and the water was removed. To each well was added 30% TFA in water (0.1 mL) and the plates were heated in an oven set to 60° C. for 1 h. The TFA solutions were removed and each bead washed with H$_2$O (4×0.1 mL). The beads were stored in 0.1 mL of water at 4° C. until use. Beads that were selected for further analysis were subjected to microsequencing.

VEGF$_{165}$ Expression and Purification

E. coli expression hosts AD494 (DE3)pLysS were transformed with a pRSET-VEGF$_{165}$ plasmid. The recombinant VEGF protein was expressed and isolated from inclusion bodies as described previously. Refolding and dimerization of the VEGF was achieved by sequential dialysis against 20 mM Tris buffer at pH 7.6 with 4 M urea and 1 mM EDTA (2×1 L), followed by buffer containing 2M urea (2×2 L), 1M urea (2×4 L), and finally buffer (2×4 L). Dimerization was confirmed by SDS-PAGE and coomassie staining under non-reducing conditions. The protein was then purified by heparin-agarose chromatography using a gradient of 0.25 to 2M NaCl in 20 mM Tris buffer at pH 7.6. The final protein was dialyzed against 20 MM Tris and 150 mM NaCl (TBS) at pH 7.6 and stored at −80° C. until use. A typical yield of 8 mg/L bacterial culture of VEGF$_{165}$ was obtained.

VEGF$_{165}$ Labeling

Approximately 1.2 mg of VEGF$_{165}$ was loaded onto a heparin-agarose column and the column washed with 0.1 M NaHCO$_3$ several times. 6-((7-amino-4-methylcoumarin-3-acetyl)amino)hexanoic acid, succinimidyl ester was diluted from a solution of DMSO into 0.1 M NaHCO$_3$. 130 µg coumerin in 1.3 mL of buffer was loaded onto the column and incubated with the VEGF$_{165}$ for 1 h at room temperature followed by 23 h at 4° C. The excess coumerin was then removed by thoroughly washing the column with TBS before eluting the protein with 20 mM Tris and 1 M NaCl at pH 7.6. The labeling of VEGF$_{165}$ was confirmed by bright spots by UV on the SDS-PAGE that corresponded to the protein visualized with Coomassie staining. The final protein was concentrated and desalted by centrifugation using VIVAspin tubes with a MWCO of 5,000 and stored at 4° C. until use. In this manner, the typical amount of labeling, estimated by UV measurements, was 4 coumerins/VEGF$_{165}$.

Screening of the library was accomplished by incubation of the beads with coumarin-labeled VEGF$_{165}$, the most common isoform of VEGF. The term VEGF includes all forms, isoforms, variations, mutants, and derivitized versions of human VEGF. VEGF$_{165}$ was expressed from E. Coli and refolded correctly to the dimeric form. The succinimidyl ester of 7-amino-4-methylcoumarin-3-acetic acid (AMCA-NHS), which has a pronounced stability to photoquenching effects, was conjugated to VEGF$_{165}$ that was preabsorbed to a heparin-agarose column. VEGF165 is retained on this column through interaction of the heparin-binding domain with heparin. Reacting the AMCA-NHS with VEGF in this way ensures that the basic residues of the heparin-binding domain do not react with the succinimidyl ester. Also, purification of the product is facile since the VEGF is only released from the column when ≧0.5 M NaCl solutions are used. Residual AMCA-NHS was removed with a low salt buffer prior to elution of the protein. The degree of labeling was estimated to be 4 coumarins per VEGF. The degree of labeling was determined from absorbance measurements of the protein-coumarin complex. Approximately 0.1 mg/mL of the labeled VEGF$_{165}$ in TBS was incubated with ~10 copies of the library, amino-PEGA beads containing no peptide, and heparin-agarose beads for 16 hours under shaking conditions. The later two served as the controls.

The beads and heparin-agarose were washed with TBS to remove unbound VEGF$_{165}$ until the amino-PEGA beads containing no peptide were non-fluorescent. The library and heparin-agarose beads were then washed successively with 20 mM Tris at pH 7.6 containing 0.25 M (2×), 0.5 M (3×), 1 M (10×), and 2 M (2×) NaCl. No fluorescently labeled VEGF$_{165}$ was observed on the heparin-agarose control beads after the 1.0 M NaCl buffer washes. Using a dissecting microscope and UV black lamp to view the library, fluorescent beads were picked out of a background of non-fluorescent beads with a micropipette and individually placed into wells of a 96-well plate. In this way, 288 beads were selected for further analysis. Since VEGF$_{165}$ is released from heparin agarose beads with 0.5–1.0 M NaCl, it was presumed that beads that fluoresce after washing with 2 M NaCl strongly bind VEGF.

Figure 5:
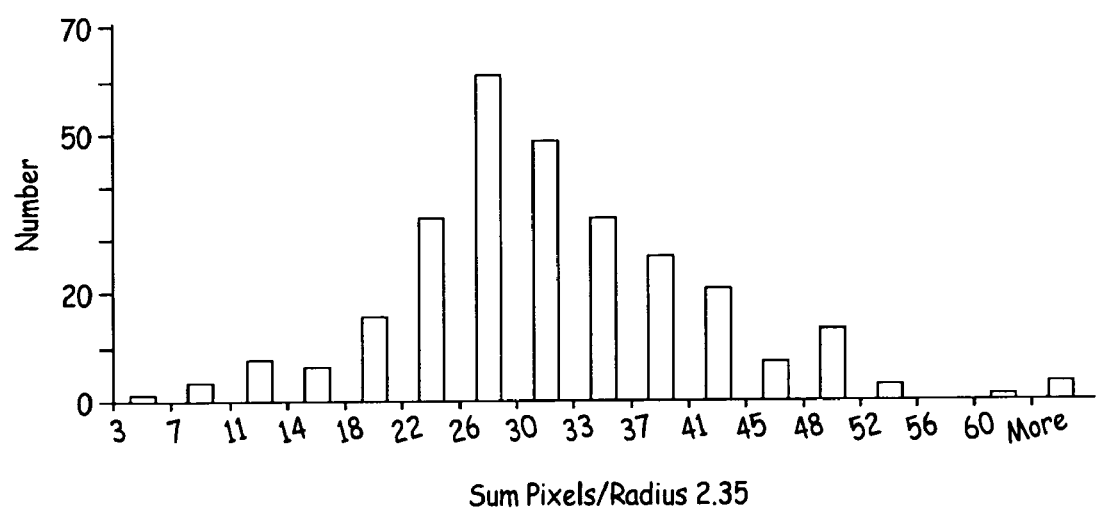
FIG. 5 depicts a histogram generated as part of the screening of the library of Example 1.

The fluorescence of each bead was quantified by imaging each individual bead on an inverted microscope equipped with a Dapi filter. The radius (r) and sum of the pixels (Σ Pix) of each bead was determined after converting the images to grayscale on Matrox Inspector. The beads were ranked according to the Σ Pix/r$^{2.35}$. The power was determined by plotting the sum of the pixels versus the radius and performing a χ2 minimization to get the best fit. Dividing by the radius to the 2.35 was necessary to account for differences in bead size and corresponding artificial differences in sum of pixel intensities. The histogram of the selected beads (FIG.5) reveals that the average value of Σ Pix/r$^{2.35}$ was 28, while several beads were significantly brighter than the rest with Σ Pix/r$^{2.35}$ of more than 60. The brightest beads (Σ Pix/r$^{2.35}$ at least 60), several beads with Σ Pix/r$^{2.35}$ values between 52 and 46, beads with the average Σ Pix/r$^{2.35}$ of 28, and a non-fluorescent bead were selected for analysis by microsequencing.

Prior to microsequencing, the beads were desulfated by heating at 60° C. in 30% TFA for 1 hour to facilitate analysis. The VEGF$_{165}$ was removed during this process, lending evidence that sulfate groups are important for binding. The coumarin was not simply quenched during the desulfating since coumarin labeled PEGA beads retained fluorescence after this process. The beads were then microsequenced. The ligands that were produced are shown in Table 1, with the ligands being ranked according to affinity as measured determining the sum of the pixels and radius from fluorescence imaging of the beads that yielded the ligands. A bead that did not retain fluorescence after washing with salt was also sequenced as a negative control (shown as 0 in Table 1.

TABLE 1

Ligands for VEGF

| Σ Pix/r$^{2.35}$ | Sequence | See SEQ ID NO: |
|---|---|---|
| 64 | Ser-Tyr(SO$_3$)-Asp-Tyr(SO$_3$) | 2 |
| 61 | Ser-Tyr(SO$_3$)-Asp-Tyr(SO$_3$) | 2 |
| 60 | Ala-Tyr(SO$_3$)-Asp-Tyr(SO$_3$) | 3 |
| 52 | Ser(Gly)-Tyr(SO$_3$)-Tyr(SO$_3$)-Phe* | 4, 5 |
| 51 | Ser-Tyr(SO$_3$)-Ala-Tyr(SO$_3$) | 6 |

TABLE 1-continued

Ligands for VEGF

| $\Sigma$ Pix/r$^{2.35}$ | Sequence | See SEQ ID NO: |
|---|---|---|
| 46 | Gly-Tyr(SO$_3$)-Ala-Tyr(SO$_3$) | 7 |
| 28 | Gly-Tyr(SO$_3$)-Val-Glu | 8 |
| 28 | Asp-Tyr(SO$_3$)-Tyr(SO$_3$)-Tyr(SO$_3$) | 9 |
| 28 | Gly-Tyr(SO$_3$)-Ser-Glu | 10 |
| 0 | Asp-Ile-Asp-Phe | — |

*The first amino acid in this sequence was unclear and could be either serine or glycine.

The most active two ranked beads were the same, SY(SO$_3$)DY(SO$_3$) (SEE SEQ ID NO: 2) and contained the groups also found in heparin, namely sulfate, carboxyl and hydroxyl functionality. The third ranked bead had a similar motif, Y(SO$_3$)-D-Y(SO$_3$) (See SEQ ID NO: 1) with an alanine instead of a serine at the amine terminus. The bead with a $\Sigma$ Pix/r$^{2\ 35}$ of 52 had S-A-Y(SO$_3$)-D-Y(SO$_3$) (SEE SEQ ID NO: 3) and those with values of 51 and 46 were very similar to each other (either serine or glycine followed by Y(SO$_3$)-A-Y(SO$_3$)). Of the three beads with average fluorescence that were sequenced, two contained one sulfated tyrosine and one contained three. The negative control was DIDF.

All of the beads sequenced that were fluorescent after washing with 2M NaCl contained at least one sulfated tyrosine. However, the negative control, although having two negatively charged aspartic acids, did not bind VEGF$_{165}$ strongly, indicating that the sulfate group per se, as opposed to the charge, enhances binding. This is a surprising result. This result is further evidenced by the observations that desulfating the peptides was necessary to remove VEGF from the beads. This data is consistent with the hypothesis that VEGF$_{165}$ is binding to the peptides through the heparin-binding domain. Nonetheless, the invention is not dependent on any particular theory of operation.

All of the most active six beads that were sequenced contained two sulfated tyrosines; in five of these beads these were in the second and fourth position. This indicates that sulfated tyrosines in the second and forth position of a tetrapeptide are motifs for strong binding. All of the fluorescent beads that were analyzed had a sulfated tyrosine in the second position suggesting that a sulfate group in this position is a motif for binding of the peptides to VEGF$_{165}$. In addition, since beads that had an average fluorescence signal either contained one sulfate or three sulfate groups versus two, the number of sulfates as well as their position may an important motif.

Sulfated tetra-peptides that bind VEGF have been invented. Peptides that bound VEGF strongly in the library screening contained two sulfated tyrosines and, typically, these were located in positions two and four of the sequence. All of the beads that were analyzed had a sulfate group in the second amino acid position, suggesting that the placement of this group is useful for binding to VEGF. These peptides may modulate VEGF activity by either inhibiting or potentiating the growth factor activity. In addition, these peptides may be incorporated into gels or polymers in order to sequester or facilitate controlled release of VEGF.

This Example demonstrates that small sulfated peptides that bind to VEGF can be produced by an embodiment employing a combinatorial library synthesis approach. The same method using the same library may be used in combination with screens for binders to other suitable targets, including heparin-binding growth factors such as bFGF and PDGF.

EXAMPLE 2

Production of Ligands for Binding ATIII

Sulfated peptides assembled into a library made according a deconvolution strategy were used to produce ligands that bind to ATIII. This Example demonstrates that small sulfated peptides that bind to ATIII can be produced by an embodiment employing a combinatorial library synthesis approach. Various positions were not varied during the library synthesis process for the sake of convenience.

Library Synthesis

The synthesis of the sulfated decapeptide libraries was performed in a FLEXCHEM 96 well reactor block (Robinson Scientific). The Fmoc/tert-Butyl or Fmoc/Boc protection strategy was used on a PEGA-resin (NOVABIOCHEM), a PEG based resin with a very low fluorescence background and well permeable for macromolecules like proteins. The methods of Example 1 were followed unless otherwise indicated. After final Fmoc-removal, the N-terminus was acetylated using acetic acid anhydride, 1-hydroxybenzotriazole (HOBt) and N,N-diisopropylethylamine (DIPEA). The protecting groups were removed using trifluoracetic acid (TFA) and water followed by the sulfation of the hydroxyl groups of the L-serine and L-tyrosine residues or the amine group of the L-lysine residues with sulfurtrioxide-pyridine complex.

Three sulfated decapeptide libraries were synthesized, with each containing only one type of sulfated residue: Ser(SO$_3$), Tyr(SO$_3$), or Lys(SO$_3$). Each library consisted of four building blocks: three hydrophobic amino acids, L-glycine, L-phenylalanine, L-valine and of the sulfated residues. Because of the hydrophobic spacing between the positively charged amino acids in heparin binding domains described by Fromm et al., a decapeptide was made. Further, amino acids in positions 2, 6 and 10 of the peptidyl-resin in the heparin mimicking decapeptides were fixed to be the sulfated residue. Positions 1–5 of the peptidyl-resin were filled with peptides in a process of splitting, coupling and mixing so that positions 1, 3, 4, and 5 each had every possible combination of the four building blocks, so that 4$^4$ different peptides (256) were made. The peptides on the peptidyl-resin were pooled and split over 64 synthesis wells of the reactor block. The last 5 positions on the peptidyl-resin amino acids were filled with amino acids, with positions 7, 8, and 9 being filled with every possible combination of the building blocks, for a total of 4$^3$ (64) combinations. Each library was thus made with 64×256=16,384 different sulfated decapeptides, with each of the libraries having the sequence of the five amino acids closest to the N-terminus as knowns. These libraries were screened and the best sub-library was picked. The best sub-library was Ac-Ser(SO$_3$)-Val-Phe-Val-Ser(SO$_3$)-Xxx-Xxx-Xxx-Ser(SO$_3$)-Xxx-PEGA (SEE SEQ ID NO: 11).

This sequence, having the five amino acids from the N-terminus of the best binding sub-library, was used to synthesize a second library, with positions 2 and 6–10 being fixed and positions 1 and 3–5 being varied. This second library was screened, in the presence of an excess of heparin, to determine the optimal sequences. The optimal sequence was the sequence Ac-Ser(SO$_3$)-Val-Phe-Val-Ser(SO$_3$)-Ser(SO$_3$)-Val-Val-Ser(SO$_3$)-Ser(SO$_3$)-PEGA (SEE SEQ ID NO: 12).

Screening

The screening of the libraries was carried out using a fluorescently labeled peptide, representing the antithrombin III heparin-binding domain. The synthesis of this peptide, N-dansyl-Gly-Lys-βAla-Phe-Ala-Lys-Leu-Ala-Ala-Arg-Leu-Tyr-Arg-Lys-Ala-NH$_2$,was performed on a PIONEER PEPTIDE SYNTHESIZER (PERCEPTIVE BIOSYSTEMS, now APPLIED BIOSYSTEMS) using standard Fmoc-chemistry.

From each of the 3 sub-libraries was taken 2 mg resin (~120 nmol peptide) and transferred into 96 filter well plates containing 100 μl PBS buffer pH 7.4. PEGA resin and heparin-agarose resin were used as control for non-specific binding and as reference. To each well was added an equal molar solution of the fluorescently labeled peptide and the resin was incubated overnight under continuously shaking. After removing the incubation solution by filtration, the resin was extensively washed until the fluorescence signal of the wells with unmodified PEGA resin was similar to that of the background. The fluorescence measurements were performed using a LS-50B luminescence spectrometer (PERKIN-ELMER) with a well plate reader at an excitation wavelength of 340 nm and an emission wavelength of 540 nm. Then the resin was incubated overnight with PBS buffer pH 7.4 containing a 5 fold molar excess of heparin (600 nmol per well) and again the resin was extensively washed. The incubation with heparin resulted in a decrease in the fluorescence signal of the heparin-agarose resin used as a control to background level. On the contrary, for certain wells with sulfated peptidyl PEGA resin a significant fluorescence signal was observed, indicating a strong binding of the heparin-binding domain peptide of antithrombin III.

The second library screening was performed as described above but 1 mg resin per well was used and the resin was incubated with the fluorescently labeled heparin-binding domain peptide of antithrombin III in the presence of a 10 fold molar excess of heparin. Thus the heparinic peptidic ligands had to compete with heparin to bind to the ATIII heparin-binding domain.

The decapeptide ligands described in this Example bound the heparin-binding domain in the presence of a 10 fold molar excess of heparin, indicating that these peptides have a high affinity ligands for the heparin-binding domain of antithrombin III. The strongest binding was found for the decapeptide with the sequence Ac-Ser(SO$_3$)-Val-Phe-Val-Ser(SO$_3$)-Ser(SO$_3$)-Val-Val-Ser(SO$_3$)-Ser(SO$_3$)-PEGA (SEE SEQ ID NO: 12). Other ATIII-binding peptides are set forth in Table 2. The heparin-mimicking characteristic of this sulfated decapeptide or its sulfonated analogs are a new class of antithrombotic agents.

TABLE 2

Additional sequences having specific binding to ATIII

| SEQUENCE | See SEQ ID NO: |
|---|---|
| Ser(SO3) Val Phe Val Ser(SO3) Xxx Xxx Xxx Ser(SO3) Xxx | 11 |
| Ser(SO3) Val Phe Val Ser(SO3) Ser(SO3) Val Val Ser(SO3) Ser(SO3) | 12 |
| Tyr(SO3) Val Val Tyr(SO3) Tyr(SO3) Xxx Xxx Xxx Tyr(SO3) Xxx | 18 |
| Ser(SO3) Val Phe Ser(SO3) Ser(SO3) Xxx Xxx Xxx Ser(SO3) Xxx | 19 |
| Se(SO3) Val Ser(SO3) Phe Se(SO3)r Xxx Xxx Xxx Ser(SO3) Xxx | 20 |
| Ser(SO3) Phe Ser(SO3) Val Ser(SO3) Xxx Xxx Xxx Ser(SO3) Xxx | 21 |
| Ser(SO3) Ser(SO3) Ser(SO3) Val Ser(SO3) Xxx Xxx Xxx Ser(S03) Xxx | 22 |
| Ser(S03) Val Phe Val Ser(SO3) Phe Val Gly Ser(SO3) Ser(SO3) | 23 |
| Ser(SO3) Val Phe Val Ser(SO3) Phe Gly Val Ser(SO3) Ser(SO3) | 24 |

EXAMPLE 3

Ligands for VEGF

This Example demonstrates that embodiments using sulfated peptides in the systems and methods of the invention produce ligands that bind with high affinities to the target VEGF, an important endothelial cell mitogen. This Example follows the methods of Example 1 unless otherwise stated.

Combinatorial Library Synthesis

A library of peptides having 7 amino acid positions was synthesized. The first three amino acids were varied using the same 9 amino acids used in Example 1. The other four amino acids of the 7 positions were fixed to be Gly-Tyr(SO$_3$)Asp-Tyr(SO$_3$), a sequence chosen from the results of the library of Example 1. The same amino acids and conditions were used to synthesize this library as for the library of Example 1, with the exception that Fmoc-Gly-Tyr(SO$_3$)Asp-Tyr(SO$_3$)-Gly-Gly-Gly-Gly-PEGA was utilized as the starting resin and the coupling was repeated a total of 3 times. The synthesis resulted in many copies of $9^3$ or 729 different peptides.

Screening Process

A colorimetric assay was used to screen the library. The assay employed two different precipitating, developing dyes. In this way, beads that bound VEGF$_{165}$ selectively and through the sulfate functionality could be determined. A portion of the library (2–3 copies) was swelled with H$_2$O and rinsed 3 times with TBS. The resin was subjected overnight to 0.1% albumin and 0.2% Tween in Tris buffered saline (TBS, blocking buffer) and then rinsed with TBS (2×) prior to adding 1 mL streptavidin alkaline phosphatase (diluted 1:1000 from a 1 mg/mL solution) and shaking for 2 hours. The resin was rinsed with TBS (5×) and 200 μL of 5-bromo-4-chloro-3-indoylphosphate p-toluidine salt/nitro blue tetrazolium chloride (BCIP/NBT) reagent was added to develop a blue/black color where the streptavidin alkaline phosphatase was present. Nonspecific adsorption of the streptavidin alkaline phosphatase was detected as blue/black stained beads. After 15 minutes, the resin was rinsed with TBS (5×) prior to adding 100 μL of about 0.25 nM of biotinylated VEGF$_{165}$ in the presence or absence of 1 or 10 equivalents of heparin sodium salt (isolated from porcine intestinal mucosa) in 400 μL of blocking buffer. The mixture was shaken overnight, the solution removed, the resin washed with TBS (6×), and 1 mL streptavidin alkaline phosphatase (diluted 1:1000 from a 1 mg/mL solution) was added. The streptavidin alkaline phosphatase preferentially attached to beads having VEGF since the VEGF was attached to biotin, which is a ligand for the streptavidin on the streptavidin alkaline phosphatase. After 2 h the solution was removed and rinsed with TBS (5×) and Fast Red substrate (PIERCE) was added to make the presence of the alkaline phosphatase visible by making a red color. Positive beads were those that were stained red. The red beads were selected, and subjected to 8M guanidine-HCl, pH=1.4 for 20 minutes prior to rinsing with H2O (3×) and DMF until residual color was removed. Desulfation of the peptides was accomplished by subjecting the resin to 30% TFA at 60° C. for 1 h. The selected beads were rinsed thoroughly with $H_2O$ and were developed by subjection to streptavidin alkaline phosphatase followed by Fast Red as described above. Beads that remained colorless after desulfation were selected and subjected to microsequencing.

Initially a very low concentration of biotinylated $VEGF_{165}$ (about 0.25 nM) was utilized to analyze the library in order to select for the strongest binders. Despite this, the results indicated that about 5–8% of the library bound $VEGF_{165}$. Therefore a competitive assay was conducted using the same low concentration of biotinylated $VEGF_{165}$ in the presence of 1 or 10 equivalents of heparin. When 1 eq. of heparin was employed, 6 beads that bound $VEGF_{165}$ via the sulfate functionality were discovered; of these 3 were sequenced. When 10 eq. of heparin were utilized, only 3 beads were selected; all of these were sequenced. The results of the microsequencing are given in Table 3. The results demonstrate that in the presence of heparin, $VEGF_{165}$ bound to the bead substituted with the peptide $Y(SO_3)Y(SO_3)GGY(SO_3)DY(SO_3)$ (SEE SEQ ID NO: 14).

TABLE 3

Ligands for binding to VEGF

| Equivalents Heparin used in Assay | Peptide Sequence | See SEQ ID NO: |
|---|---|---|
| 1 | $FY(SO_3)GGY(SO_3)DY(SO_3)$ | 13 |
| 1 | $Y(SO_3)Y(SO_3)GGY(SO_3)DY(SO_3)$ | 14 |
| 1 | $Y(SO_3)[A]Y(SO_3)GGY(SO_3)DY(SO_3)$* | 14, 15 |
| 10 | $Y(SO_3)Y(SO_3)GGY(SO_3)DY(SO_3)$ | 14 |
| 10 | $Y(SO_3)Y(SO_3)GGY(SO_3)DY(SO_3)$ | 14 |
| 10 | $Y(SO_3)Y(SO_3)GGY(SO_3)DY(SO_3)$ | 14 |

*The first amino acid is either A or $Y(SO_3)$.

The sequence from the highest ranked bead from the first library of Example 1, was synthesized as $SY(SO_3)DY(SO_3)G$ (SEE SEQ ID NO: 17), and the peptide $Y(SO_3)Y(SO_3)GGY(SO_3)DY(SO_3)$ (SEE SEQ ID NO: 14) from the library of this Example were both synthesized independently and the dissociation constant ($K_D$) determined by surface plasma resonance (SPR). The peptides were compared to suramin, a known heparin mimic that inhibits angiogenesis. SPR allows for the direct comparison of affinities of the three compounds, and the results are given in Table 4. The results demonstrate that both $SY(SO_3)DY(SO_3)G$ (SEE SEQ ID NO: 17) and $Y(SO_3)Y(SO_3)GGY(SO_3)DY(SO_3)$ (SEE SEQ ID NO: 14) bind to VEGF with much higher affinity than suramin, with the later being the strongest binder. Using SPR, there was no detectible binding of the analogous desulfated peptides to VEGF.

TABLE 4

Dissociation Constants ($K_D$ written as ± standard deviation).

| Compound | $K_D$ | See SEQ ID NO: |
|---|---|---|
| Suramin | 340 µM ± 100 µM | — |
| $SY(SO_3)DY(SO_3)G$ | 3.1 µM ± 0.7 µM | 17 |
| $Y(SO_3)Y(SO_3)GGY(SO_3)DY(SO_3)G$ | 140 nM ± 35 nM | 16 |

REFERENCES

Alberts et al., *Molecular Biology of the Cell*, $2^{nd}$ edition.

Al-Obeidi et al., 1998.

Banerjee R. "Liposomes: applications in medicine". *J Biomater Appl*. 2001 July; 16(1):3–21.

Bentolila et al. (2000). "Synthesis and Heparin-like biological activity of amino acid-based polymers. *Polymers for advanced technologies*. 11:377–387.

Blondelle, S. E., Takahashi, E., Dinh, K. T. & Houghten, R. A. (1995). "The antimicrobial activity of hexapeptides derived from synthetic combinatorial libraries". *Journal of Applied Biotechnology*, 78, 39.

Brandl M. "Liposomes as drug carriers: a technological approach". *Biotechnol Annu Rev*". 2001;7:59–85.

Burgess, K., Linthicum, D. S. & Shin, H. W. (1995). "Solid-phase syntheses of unnatural biopolymers containing repeating urea units". *Angewandte Chemie* (International Edition in English), 34, 907.

Bussemer T, Otto I, Bodmeier R. "Pulsatile drug-delivery systems". *Crit Rev Ther Drug Carrier Syst*. 2001;18(5): 433–58.

Campos, Socorro Vázquez et al. (2002) "Preparation of novel O-sulfated amino acid building blocks with improved acid stability for Fmoc-based solid-phase peptide." *The Royal Society of Chemistry*, 682–686.

Cho, C. Y., Moran, E. J., Cherry, S. R., Stephans, J. C., Fodor, S. P. A., Adams, C. L., Sundaram, A., Jacobs, J. W. & Schultz, P. G. (1993). "An unnatural biopolymer". *Science*, 261, 1303.

Chorny M, Fishbein I, Golomb G. "Drug delivery systems for the treatment of restenosis". *Crit Rev Ther Drug Carrier Syst*. 2000; 17(3):249–84.

Cleland J L. "Protein delivery from biodegradable microspheres" (1997). *Pharm Biotechnol*. 1997; 10:1–43.

de Bont, D. B. A., Moree, W. J. & Liskamp, R. M. J. (1996). "Molecular diversity of peptidomimetics: approaches to the solid phase synthesis of peptidosulfonamides". *Bioorganic Medicinal Chemistry*, 4, 667.

Deprez, B., Williard, X., Bourel, L., Coste, H., Hyafil, F. & Tartar, A. (1995). "Orthogonal combinatorial chemical libraries". *Journal of the American Chemical Society*, 117, 5405.

de Raucourt E, Mauray S, Chaubet F, Maiga-Revel O, Jozefowicz M and Fischer A. "Anticoagulant activity of dextran derivatives". 1998.

Devlin, J. J., Panganiban, L. C. & Devlin, P. E. (1990). "Random peptide libraries. A source of specific protein binding molecules". *Science*, 249, 404.

DeWitt, S. H. H., Kiely, J. K., Stankovic, C. J., Schroeder, M. C., Cody, D. M. R. & Pavia, M. R. (1993). "'Diversomers': an approach to nonpeptide, nonoligomeric chemical diversity". *Proceedings of the National Academy of Sciences, USA*, 90, 6909.

Dooley C. T. & Houghten, R. A., (1993). "The use of positional scanning synthetic peptide combinatorial libraries for the rapid determination of opioid receptor ligands". *Life Sciences*. 56, 1509.

Duncan R. "Drug-polymer conjugates: potential for improved chemotherapy". *Anticancer Drugs*. 1992 June; 3, 3.

Eppstein D A, Longenecker J P. "Alternative delivery systems for peptides and proteins as drugs". *Crit Rev Ther Drug Carrier Syst*. 1988;5(2):99–139.

Erb, E., Janda, K. & Brenner, S. (1994). "Recensive deconvolution of combinatorial chemical libraries". *Proceedings of the National Academy of Sciences*, 91, 11422.

Ettenson D S, Edelman E R. "Local drug delivery: an emerging approach in the treatment of restenosis". *Vasc Med*. 2000;5(2):97–102.

Feret B. "A novel synthetic antithrombotic for prevention of venous thromboembolism". Formulary. 2001 December (36).

Fix J A. "Oral controlled release technology for peptides: status and future prospects". *Pharm Res*. 1996 December; 13(12):1760–4.

Fodor, S. P. A., Read, J. L., Pirrung, M. C., Stryer, L., Lu, A. T. & Solas, D. (1991). "Light-directed, spatially addressable parallel chemical synthesis". *Science*, 251, 767.

Folkman J., Weisz P, Joullie M, Li W. and Ewing W. "Control of angiogenesis with synthetic heparin substitutes". *Science*. 1989 March; 241.

Frank, R. (1992). "Spot-synthesis: an easy technique for the positionally addressable, parallel chemical synthesis on a membrane support". *Tetrahedron*, 48, 9217.

Fromm, J. R., Hileman, R. E., Caldwell, E. E. O., Weiler, J. M., & Linhardt (1997). "Pattern and spacing of basic amino acids in heparin binding sites". *Arch. Biochem. Biophys.*, 1, 343.

Gennari, C., Nestler, H. P., Salom, B. & Still, W. C. (1995). "Synthetic receptors based on vinylogous sulphonyl peptides". *Angewandte Chemie* (International Edition in English), 34, 1765.

Geysen, H. M., Melven, R. H., & Barteling, S. J. (1984). "Use of peptide synthesis to probe viral antigens for epitopes to a resolution of a single amino acid". *Proceedings of the National Academy of Sciences, USA*, 81, 3998.

Gonda I. "The ascent of pulmonary drug delivery". *J Pharm Sci*. 2000 July;89(7):940–5.

Grabow T S, Derdzinski D, Staats P S. "Spinal drug delivery". *Curr Pain Headache Rep*. 2001 December;5(6):510–6.

Groothuis D R. "The blood-brain and blood-tumor barriers: a review of strategies for increasing drug delivery". *Neuro-oncol*. 2000 January;2(1):45–59.

Han, H. & Janda, K. D. (1996). "Azatides: solution and liquid phase syntheses of a new peptidomimetics". *Journal of the American Chemical Society*, 118, 2539.

Haroun R I, Brem H. "Local drug delivery". *Curr Opin Oncol*. 2000 May;12(3): 187–93.

Hatefi A, Amsden B. "Biodegradable injectable in situ forming drug delivery systems". *J Control Release*. 2002 Apr. 23;80(1–3):9–28.

Herbert J M, Herault J P, Bernat A, van Amsterdam R G M, Lormeau J C, Petitou M, van Boeckel C, Hoffmann P, and Meuleman D G. "Biochemical and Pharmacological Properties of SANORG 34006, a potent and long-acting synthetic pentasaccharide". Blood. Jun. 1, 1998; 91(11): 4197–4205.

Herbert J M, Herault J P, Bernat A, van Amsterdam R G M, Vogel, G M T, Lormeau J C, Petitou M, and Meuleman D G. "Biochemical and Pharmacologica Properties of SANORG 32701".American Heart Association. 1996; 590–600.

Houghten, R. A.; Pinilla, C.; Blondelle, S. E.; Appel, J. R.; Dooley, C. T.; Cuervo, J. H. (1991). "Generation and use of synthetic peptide combinatorial libraries for basic research and drug discovery". *Nature*, 354, 84.

Hussain N. "Ligand-mediated tissue specific drug delivery". *Adv Drug Deliv Rev*. 2000 Sep. 30;43(2–3):95–100. No abstract available.

Hyon S H. "Biodegradable poly (lactic acid) microspheres for drug delivery systems". *Yonsei Med J*. 2000 December;41(6):720–34.

Jabbal-Gill I, Lin W, Kistner O, Davis S S, Illum L. "Polymeric lamellar substrate particles for intranasal vaccination". *Adv Drug Deliv Rev*. 2001. 51(1–3):97–111.

Kawasaki, G. (1991) "Cell-free synthesis and isolation of novel genes and polypeptides". PCT International Patent Application WO91/05058.

Khmelnitsky, Y. L., Michels, P. C., Dordick, J. S., & Clark, D. S. (1996). "Generation of solution phase libraries or organic molecules by combinatorial biocatalysis". In *Molecular Diversity and Combinatorial Chemistry*. Chaiken, I. M., Janda, K. D. (eds), p. 145. American Chemical Society: Washington, D.C.

Khosla, C. & Zawada, R. J. X. (1996). "Generation of polyketide libraries via combinatorial biosynthesis". *Trends in Biotehcnology*, 14, 335.

Krafft M P. "Fluorocarbons and fluorinated amphiphiles in drug delivery and biomedical research". *Adv Drug Deliv Rev.*, 2001 Apr. 25;47(2–3):209–28.

Kumar, 2000.

Lam, K. S. & Lebl, M. (1996). "Combinatorial library based on the one-bead-one-compound concept". In *Peptide and Non-Peptide Libraries: A handbook*. Jung, G. (ed.), p. 173. VCH Publisher: Weinheim.

Lametal., 1991.

Lam, K. S., Lebl, M. & Krchnak, V. (1997). "The 'one-bead-one-compound' combinatorial library method". *Chemical Reviews*, in press.

Lam, K. S. (1997). "Application of combinatorial library methods in cancer research and drug discovery". *Anticancer drug design*, 12.

Langer R, Moses M. "Biocompatible controlled release polymers for delivery of polypeptides and growth factors". *J Cell Biochem*. 1991 April;45(4):340–5.

Lavasanifar A, Samuel J, Kwon G S. "Poly(ethylene oxide)-block-poly(L-amino acid) micelles for drug delivery". *Adv Drug Deliv Rev*. 2002 Feb. 21;54(2): 169–90.

Lehr C M. "Bioadhesion technologies for the delivery of peptide and protein drugs to the gastrointestinal tract". *Crit Rev Ther Drug Carrier Syst*. 1994; 11(2–3): 119–60.

Liekens S, Leali D, Neyts J, Esnouf R, Rusnati M, Dell'era P, Maudgal P, DeClercq E, and Presta M. "Modulation of fibroblast growth factor-2 receptor binding, signaling, and mitogenic activity by heparin-mimicking polysulfonated compounds". *Molecular Pharmacology*. 1999; 56(204–213).

Lo E H, Singhal A B, Torchilin V P, Abbott N J. "Drug delivery to damaged brain". *Brain Res Brain Res Rev*. 2001 December;38(1–2):140–8.

Logeart-Avramoglou, D and Jozefonvicz J. "Carboxymethyl Benzylamide Sulfonate Dextrans (CMDBS), a family of biospecific polymers endowed with numerous biological properties: a review". 1999.

Meers P. "Enzyme-activated targeting of liposomes". *Adv Drug Deliv Rev*. 2001 Dec. 31;53(3):265–72.

Miao et al., "Modulation of Fibroblast Growth Factor-2 Receptor Binding, Dimerization, Signaling, and Angiogenic Activity by a Synthetic Heparin-mimicking Polyanioinc Compound". *J. Clin. Invest*. April 1997; 99(7): 1565–1575.

Muller M. "Microdialysis in clinical drug delivery studies". *Adv Drug Deliv Rev*. 2000 Dec. 15;45(2–3):255–69.

Muramatsu, R., Sasaki, M., Watanabre, N., Goto, Y., Okayama, T., Nukui, E., Morikawa, T. and Hayashi, H. (1997). "Antithrombotic effect of NF-6505, a novel anion-binding eosite inhibitor". *Thrombosis Research*, 6, 86.

Okada H, Toguchi H. "Oral controlled release technology for peptides: status and future prospects". *Pharm Res*. 1995 December; 13, 12.

Parish C, Freeman C, Brown K, Francis D, and Cowden W. "Identification of sulfated oligosaccharide-based inhibitors of tumor growth and metastasis using novel in vitro assays for angiogenesis and heparanase activity". *Cancer Research*. 1999 Jul. 15; (59) 3433–3441).

Park J W. "Liposome-based drug delivery in breast cancer treatment". *Breast Cancer Res*. 2002;4(3):95–9.

Parmley S. F. & Smith G. P., (1988) "Antibody-selectable filamentous fd phage vectors: affinity purification of target genes". *Gene*, 73, 305.

Pillai O, Panchagnula R. "Polymers in drug delivery". *Curr Opin Chem Biol*. 2001 August;5(4):447–51.

Pillai O, Dhanikula A B, Panchagnula R. "Drug delivery: an odyssey of 100 years". *Curr Opin Chem Biol*. 2001 August;5(4):439–46.

Pirrung and Chen, 1995.

*Polymer Handbook*, 4$^{th}$ edition, by J. Brandrup et al.

Qiu Y, Park K. "Environment-sensitive hydrogels for drug delivery". *Adv Drug Deliv Rev*. 53, 3.

Ravi Kumar M N. "Nano and microparticles as controlled drug delivery devices". *J Pharm Pharm Sci*. 2000 May–August;3(2):234–58.

Regar E, Sianos G, Serruys P W. "Stent development and local drug delivery". *Br Med Bull*. 2001;59:227–48.

Sanders L M. "Drug delivery systems and routes of administration of peptide and protein drugs". 1990 April-June; 15(2):95–102.

Schatz, P. J. (1993). "Use of peptide libraries to map the substrate specificity of a peptide-modifying enzyme: a 13 residue consensus peptide specifies biotinylation in Escherichia coli". *Biotechnology*, 11, 1138.

Senel S, Kremer M, Nagy K, Squier C. "Delivery of bioactive peptides and proteins across oral (buccal) mucosa". 2001 June;2(2):175–86.

Simon, R. J., Kaina, R. S., Zuckermann, R. N., Huebner, V. D., Jewell, D. A., Banville, S., Ng, S., Wang, L., Rosenberg, S., Marlowe, C. K., Spellmeyer, D. C., Tan, R., Frankel, A. D., Santi, D. V., Cohen, F. E. & Bartlett, P. A., (1992). "Peptoids: a modular approach to drug discovery". *Proceedings of the National Academy of Sciences, USA*, 89, 9367.

Sinha V R, Kaur M P. "Permeation enhancers for transdermal drug delivery". *Drug Dev Ind harm*. 2000 November; 26(11):1131–40.

Songyang, Z., Shoelson, S. E., Chandhuri, M., Gish, G., Pawson, T., Haser, W., King, F., Roberts, T., Ratnofsky, S., Lechleider, R. J., Neel, B. G., Birge, R. B., Fajardo, J. E., Chou, M. M., Hanafusa, H., Schaffhausen, B. & Cantley, L. C. (1993). "SH$_2$ domains recognize specific phosphopeptide sequences". *Cell*, 72, 767.

Songyang, Z., Carrway, K. L., III, Eck, M. J., Harrison, S. C., Feldman, R. A., Modammadi, M., Schlessinger, J., Hubbard, S. R., Smith, D. P., Eng, C., Lorenzo, M. J., Ponder, B. A. J. Mayer, B. J. & Cantley, L. C. (1995). "Cataltyic specificity of protein tyrosine kinases is critical for selective signaling". *Nature*, 373, 536.

Sood A, Panchagnula R. "Peroral route: an opportunity for protein and peptide drug delivery". *Chem Rev*. 101, 11. No abstract available.

Soppimath K S, Aminabhavi T M, Kulkarni A R, Rudzinski W E. "Biodegradable polymeric nanoparticles as drug delivery devices". *J Control Release*. 2001 Jan. 29;70 (1–2):1–20.

Stryer, Biochemistry, 3$^{rd}$ edition.

Thompson, L. A. & Ellman, J. A. (1996). "Synthesis and applications of small molecule libraries". *Chemistry Review*, 96, 555.

Torchilin V P. "Structure and design of polymeric surfactant-based drug delivery systems". *J Control Release*. 2001 Jun. 15;73(2–3):137–72.

van Boeckel C and Petitou M. "The unique antithrombin III binding domain of heparin: a lead to the new synthetic antithrombotics". *Angewandte Chemie*. 1993 December. 32(12):1671–1818.

Vandamme T F. "Microemulsions as ocular drug delivery systems: recent developments and future challenges". *Prog Retin Eye Res*. 2002 January;21(1):15–34.

Verma R K, Mishra B, Garg S. "Osmotically controlled oral drug delivery". *Drug Dev Ind Pharm*. 2000 July;26(7): 695–708.

Verma R K, Krishna D M, Garg S. "Formulation aspects in the development of osmotically controlled oral drug delivery systems". *J Control Release*. 2002 Feb. 19;79 (1–3):7–27.

Vyas S P, Singh A, Sihorkar V. "Ligand-receptor-mediated drug delivery: an emerging paradigm in cellular drug targeting". *Crit Rev Ther Drug Carrier Syst*. 2001;18(1): 1–76.

Zimmer R, Ashburn M A. "Noninvasive drug delivery". *Compr Ther*. 2001 Winter;27(4):293–301.

Zugmaier G, Lippman M, and Wellstein A. "Inhibition by pentosan polysulfate (PPS) of heparin-binding growth factors released from tumor cells and blockage by PPS of tumor growth in Animals". Journal of the National Cancer Institute. 1992 Nov. 18; 84(22):1716–1724.

We claim:

1. A ligand for binding a target biomolecule, the ligand comprising
a peptide having at least one sulf(on)ated amino acid and at least one amino acid chosen from the group consisting of neutral and positively charged amino acid,
wherein the ligand has a $K_D$ for the target biomolecule of less than about 600 μM in physiological solution and specifically binds to at least one heparin binding site of the target biomolecule,
wherein the pentide comprises a sequence that includes derivitized SEQ ID NO: 1, wherein the tyrosines of derivitized SEQ ID NO: 1 are either sulfonated or sulfated.

2. The ligand of claim 1, wherein the Kd is less than about 60 μM.

3. The ligand of claim 1, comprising at least two sulf(on) ated amino acids.

4. The ligand of claim 1, with the peptide having at least one hydrophobic amino acid.

5. The ligand of claim 1 wherein at least one amino acid of derivitized SEQ ID NO: 1 is conservatively substituted.

6. The ligand of claim 1 wherein the derivitized sequences have at least one conservative substitution.

7. The ligand of claim 1 wherein the target of the ligand is VEGF.

8. The ligand of claim 7 wherein the peptide comprises a member of the group consisting of sulf(on)ated derivatives of Ser, Tyr, Thr, and Lys.

9. The ligand of claim 1 wherein the peptide further comprises a member of the group consisting of sulf(on)ated derivatives of Ser, Tyr, Thy, and Lys.

10. The ligand of claim 1, wherein the ligand is associated with a delivery vehicle for delivering the ligand to a patient.

11. The ligand of claim 10 wherein the delivery vehicle is a liposome.

12. A method for binding a heparin-binding biological target with a ligand, the method comprising exposing the ligand of claim 1 to the target.

13. The method of claim 12 wherein the exposing is performed by injecting the ligand into a patient.

14. The method of claim 13 wherein the injection is chosen from the group of injections consisting of subdermal, intramuscular and peritoneal.

15. The method of claim 12 further comprising associating the ligand with a delivery vehicle.

* * * * *

UNITED STATES PATENT AND TRADEMARK OFFICE
CERTIFICATE OF CORRECTION

PATENT NO. : 7,060,681 B2  Page 1 of 1
APPLICATION NO. : 10/201547
DATED : June 13, 2006
INVENTOR(S) : Jeffrey A. Hubbell, Ronald Schoenmakers and Heather D. Maynard It is certified that error appears in the above-identified patent and that said Letters Patent is hereby corrected as shown below:

On Title page item 56
Page 1, column 2, Other Publications column, delete "Antitbrombotics" and insert --Antithrombotics--.

Page 1, column 2, Other Publications column, delete "Hërault" and insert --Hérault--.

Page 27, Claim 1, line 11, delete "pentide", and insert --peptide--.

Page 27, Claim 9, line 8, delete "Thy", and insert --Thr--.

Page 27, Claim 14, line 20, after "intramuscular" insert --,--.

Signed and Sealed this

Thirteenth Day of March, 2007

JON W. DUDAS
*Director of the United States Patent and Trademark Office*